(12) United States Patent
Konakai et al.

(10) Patent No.: US 10,564,071 B2
(45) Date of Patent: Feb. 18, 2020

(54) METHOD AND SYSTEM FOR INSPECTING DAMPING FORCE VARIABLE MECHANISM, AND METHOD FOR INSPECTING PRESSURE DAMPING DEVICE

(71) Applicants: Showa Corporation, Gyoda (JP); Honda Motor Co., Ltd., Tokyo (JP)

(72) Inventors: Seiryo Konakai, Gyoda (JP); Ken Issiki, Haga-gun (JP); Ryoma Kanda, Wako (JP); Yukihiro Orimoto, Wako (JP); Koichi Shibusawa, Wako (JP); Tomohiro Yamazaki, Wako (JP)

(73) Assignees: Showa Corporation, Gyoda (JP); Honda Motor Co., Ltd., Tokyo (JP)

(*) Notice: Subject to any disclaimer, the term of this patent is extended or adjusted under 35 U.S.C. 154(b) by 450 days.

(21) Appl. No.: 15/313,943

(22) PCT Filed: Feb. 2, 2015

(86) PCT No.: PCT/JP2015/052881
§ 371 (c)(1),
(2) Date: Nov. 23, 2016

(87) PCT Pub. No.: WO2015/182168
PCT Pub. Date: Dec. 3, 2015

(65) Prior Publication Data
US 2017/0199103 A1 Jul. 13, 2017

(30) Foreign Application Priority Data

May 28, 2014 (JP) ................................. 2014-109709
May 28, 2014 (JP) ................................. 2014-110665

(51) Int. Cl.
*G01M 17/04* (2006.01)
*G01N 29/12* (2006.01)
*G07C 5/08* (2006.01)

(52) U.S. Cl.
CPC ............ *G01M 17/04* (2013.01); *G01N 29/12* (2013.01); *G07C 5/0808* (2013.01); *B60G 2400/518* (2013.01)

(58) Field of Classification Search
CPC ....... G01M 17/04; G01N 29/12; G01N 29/14; G01N 29/4436; B60G 17/08; F16F 9/32; G07C 5/0808
See application file for complete search history.

(56) References Cited

U.S. PATENT DOCUMENTS 4,589,273 A * 5/1986 Tamasi .................. G01M 17/04
73/11.08
4,761,991 A 8/1988 Femböck
(Continued)

FOREIGN PATENT DOCUMENTS

CN       86108430 A    7/1987
CN       1743829 A     3/2006
(Continued)

OTHER PUBLICATIONS

Office Action dated Jun. 27, 2018 for the corresponding Chinese Patent Application No. 201580028349.9.
(Continued)

*Primary Examiner* — David Z Huang
(74) *Attorney, Agent, or Firm* — Leason Ellis LLP

(57) ABSTRACT

Provided is an examination method for a damping force variable mechanism, the examination method including: an operation step of operating a damper in a state in which the damper is installed in a vehicle, the damper being provided with a damping force variable mechanism that changes a damping force according to an input current (an example of a signal); and a detection step of detecting an induction current (an example of an output from the vehicle) from the damping force variable mechanism of the damper installed in the vehicle, wherein a detection device that performs the
(Continued)

operation of the detection step is provided. Thus, the damping force variable mechanism of a pressure damping device can be examined in a state in which the damping force variable mechanism is installed in the vehicle.

20 Claims, 19 Drawing Sheets

(56) References Cited

U.S. PATENT DOCUMENTS

| | | | |
|---|---|---|---|
| 2005/0241366 A1* | 11/2005 | Sonnenburg | G01M 17/04 73/11.04 |
| 2006/0229791 A1 | 10/2006 | Oblizajek et al. | |
| 2007/0044537 A1 | 3/2007 | Knox | |
| 2008/0179842 A1 | 7/2008 | Jee | |
| 2009/0312966 A1* | 12/2009 | Nobis | G01M 17/04 702/56 |
| 2011/0218707 A1 | 9/2011 | Inoue et al. | |
| 2012/0073920 A1 | 3/2012 | Yamasaki et al. | |
| 2013/0328277 A1* | 12/2013 | Ryan | B60G 17/016 280/5.519 |
| 2014/0291943 A1* | 10/2014 | Murakami | B60G 17/016 280/5.514 |
| 2016/0243916 A1* | 8/2016 | Kubota | B60G 17/015 |

FOREIGN PATENT DOCUMENTS

| | | |
|---|---|---|
| CN | 101235861 A | 8/2008 |
| DE | 102011100313 A | 11/2012 |
| JP | 78-82901 U | 7/1978 |
| JP | 87-099409 U | 6/1987 |
| JP | 4-32741 A | 2/1992 |
| JP | 07-35654 A | 7/1995 |
| JP | 07-186669 A | 7/1995 |
| JP | 09-264820 A | 7/1997 |
| JP | 2013-015163 A | 2/2007 |
| JP | 2007-64969 A | 3/2007 |
| JP | 2012-072857 A | 4/2012 |
| WO | WO-2010-064291 A | 6/2010 |

OTHER PUBLICATIONS

Office Action dated Aug. 24, 2018 for the corresponding German Patent Application No. 112015002514.6.
International Search Report dated Apr. 28, 2015 for the corresponding PCT Application No. PCT/JP2015/052881.
Office Action dated Oct. 23, 2018 for the corresponding Japanese Patent Application No. 2016-523168.
Office Action dated Feb. 27, 2019 for the corresponding Chinese Patent Application No. 201580028349.9 (an English translation attached hereto).

* cited by examiner

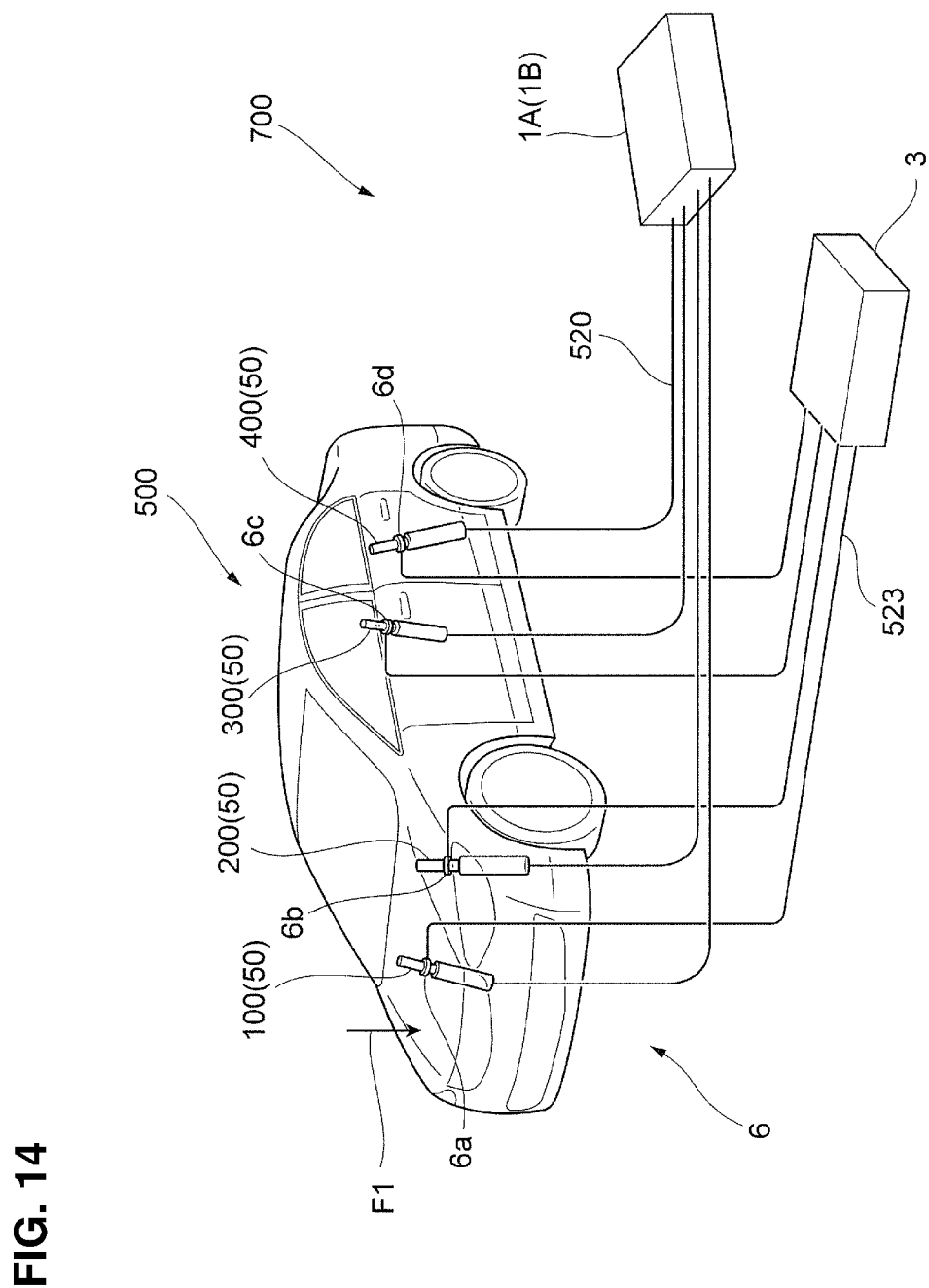

FIG. 15

| | EXAMPLE 1 | EXAMPLE 2 | EXAMPLE 3 |
|---|---|---|---|
| CHANGE IN CURRENT [A] | 0.3~1.6 | 0.3~1.6 | 0.3~0.8 |
| FREQUENCY [Hz] | 5 | 10 | 10 |
| HAND FEELING (PRESSURE SENSE) | DEFINITE DIFFERENCE | DEFINITE DIFFERENCE | SMALL BUT DEFINITE DIFFERENCE |
| HAMMERING SOUND (AUDITORY SENSE) | AUDIBLE | AUDIBLE | SMALL BUT AUDIBLE |
| DETERMINATION | POSSIBLE | POSSIBLE | POSSIBLE |

(HAND FEELING and HAMMERING SOUND rows labeled: DIFFERENCE BETWEEN INPUT CURRENT AND CONSTANT CURRENT)

METHOD AND SYSTEM FOR INSPECTING DAMPING FORCE VARIABLE MECHANISM, AND METHOD FOR INSPECTING PRESSURE DAMPING DEVICE

CROSS-REFERENCE TO RELATED PATENT APPLICATIONS

This application is a U.S. National Phase Application under 35 U.S.C. § 371 of International Patent Application No. PCT/JP2015/052881, filed Feb. 2, 2015, and claims the benefit of Japanese Patent Applications No. 2014-110665, filed May 28, 2014 and No. 2014-109709, filed May 28, 2014, all of which are incorporated by reference herein in their entireties. The International Application was published in Japanese on Dec. 3, 2015 as International Publication No. WO/2015/182168 under PCT Article 21(2).

FIELD OF THE INVENTION

The present invention relates to an examination method and an examination system for a damping force variable mechanism and an examination method for a pressure damping device.

DESCRIPTION OF THE RELATED ART

Pressure damping devices installed in vehicles to reduce vibrations input to the vehicles have been known. As such, some are provided with a damping force variable mechanism capable of varying a damping force (see, for example, Patent Document 1 and Patent Document 2).

CITATION LIST

Patent Document

Patent Document 1: JP-2012-72857-A
Patent Document 2: JP-2013-15163-A

SUMMARY OF THE INVENTION

Problem that the Invention is to Solve

Meanwhile, when an examination as to whether a damping force variable mechanism normally operates is conducted, a pressure damping device is removed from a vehicle and then put in dedicated examination equipment or the like to be examined That is, in order to examine the pressure damping device, the pressure damping device is required to be removed from the vehicle to be examined separately.

However, it greatly takes time and effort to remove the pressure damping device from the vehicle every time the examination is conducted and install the pressure damping device in the vehicle again after the examination.

The present invention has an object of providing an examination method and an examination system for a damping force variable mechanism and an examination method for a pressure damping device that allow the examination of the damping force variable mechanism of the pressure damping device in a state in which the damping force variable mechanism is installed in a vehicle.

Means for Solving the Problem

An embodiment of the present invention provides an examination method for a damping force variable mechanism, the examination method including: an operation step of operating a pressure damping device in a state in which the pressure damping device is installed in a vehicle, the pressure damping device being provided with a damping force variable mechanism that changes a damping force according to an input signal; and a detection step of detecting a change occurring in the vehicle due to the operation step.

In addition, another embodiment of the present invention provides an examination system for a damping force variable mechanism, the examination system including: a detection device that detects an output from a vehicle when a pressure damping device is operated in a state in which the pressure damping device is installed in the vehicle, the pressure damping device being provided with a damping force variable mechanism that changes a damping force according to an input signal.

According to the examination method and the examination system for the damping force variable mechanism of the present invention, the output from the vehicle is detected when the pressure damping device is operated in a state in which the pressure damping device is installed in the vehicle. The output from the vehicle changes when the damping force variable mechanism normally operates. By the detection of a change in the output from the vehicle, an examination as to whether the damping force variable mechanism normally operates is allowed in a state in which the pressure damping device is installed in the vehicle.

Moreover, still another embodiment of the present invention provides an examination method for a pressure damping device of a vehicle having a damping force variable mechanism that changes a damping force according to an input signal, the examination method including: an application step of periodically applying a signal at a frequency between a sprung resonance frequency and a lower one of an unsprung resonance frequency and a response frequency of the pressure damping device to the damping force variable mechanism in a state in which the pressure damping device is installed in the vehicle; an oscillation step of oscillating the vehicle so as to operate the dumping-force variable mechanism while the signal is applied to the damping force variable mechanism in the application step; and a detection step of detecting a vibration state of the vehicle, wherein a plurality of types of signals having different amplitudes is successively applied in the application step, and a change in the vibration state of the vehicle is detected according to a change in the plurality of types of signals in the detection step.

Advantageous Effects of Invention

According to an embodiment of an examination method and an examination system for a damping force variable mechanism and an examination method for a pressure damping device, it is possible to examine the damping force variable mechanism of the pressure damping device in a state in which the pressure damping device is installed in a vehicle.

BRIEF DESCRIPTION OF THE DRAWINGS

FIG. 14 is a schematic view showing the examination system of a variation to which a damper stroke detection device is applied as a detection device;

FIG. 15 is a table showing a list of experimental results in which, compared with a case in which a constant current was input to the damping force variable mechanism, a difference in pressure sense and a difference in auditory sense were verified for each of the different combinations of changes in a current input to the damping force variable mechanism and frequencies accompanied by the changes;

DETAILED DESCRIPTION OF THE INVENTION

Hereinafter, a description will be given, with reference to the drawings, of the embodiments of an examination method and an examination system for the damping force variable mechanism of a pressure damping device according to the present invention.

First Embodiment (Configuration)

Figure 1:
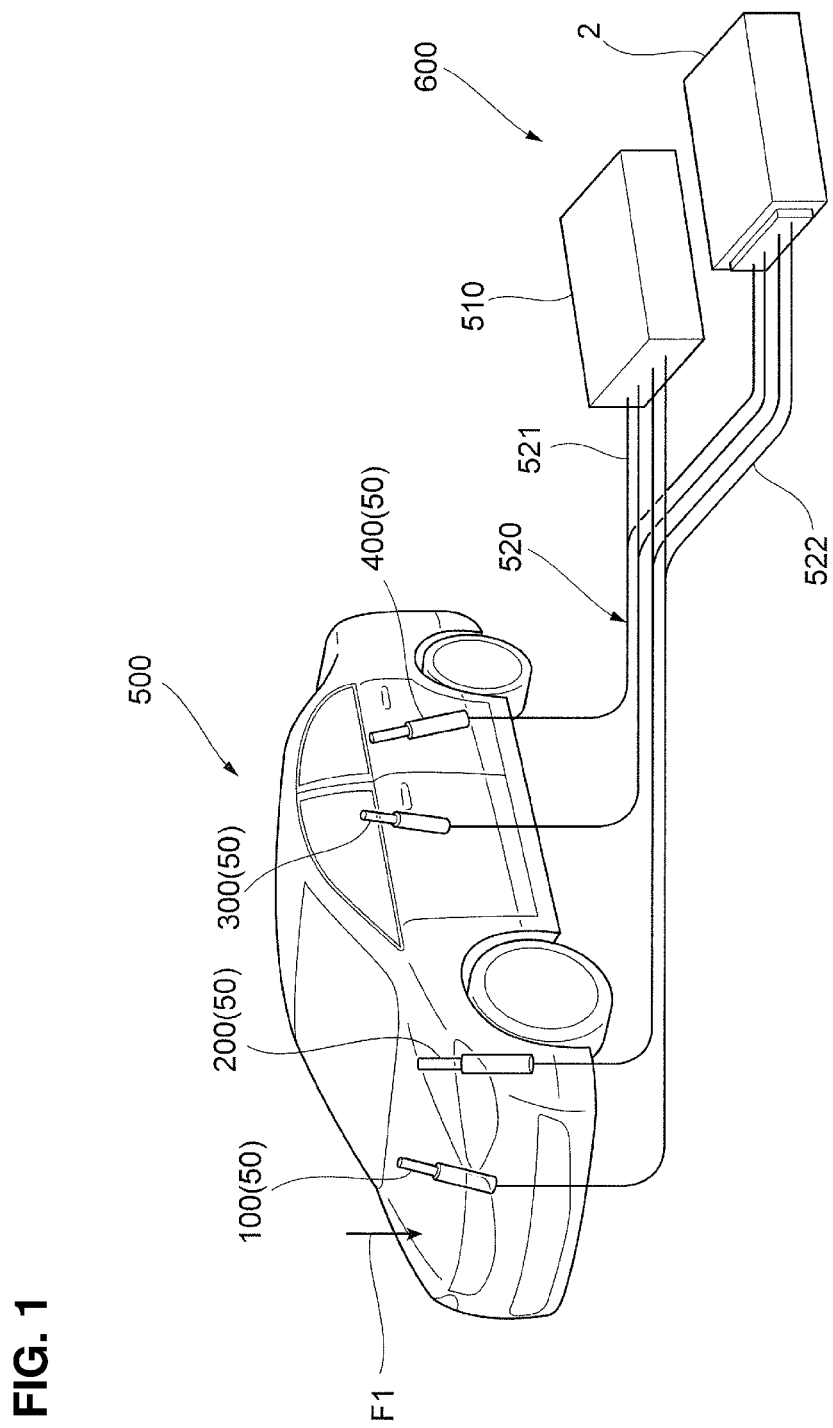
FIG. 1 is a schematic view showing an examination system for a damping force variable mechanism in a damper according to a first embodiment of the present invention.

FIG. 1 is a schematic view showing the configuration of an examination system 600 for damping force variable mechanisms 50 of dampers 100, 200, 300, and 400 according to a first embodiment of the present invention. As shown in FIG. 1, each of the dampers 100, 200, 300, and 400 is installed corresponding to each of the wheels of a vehicle 500.

(Configuration of Dampers 100, 200, 300, and 400)

First, the dampers 100, 200, 300, and 400 as examination targets in the first embodiment will be described. Note that since the dampers 100, 200, 300, and 400 are common in their basic structures, the damper 100 will be described below as a representative of the dampers 100, 200, 300, and 400.

The dampers 100, 200, 300, and 400 are common in all embodiments that will be described later.

Figure 2:
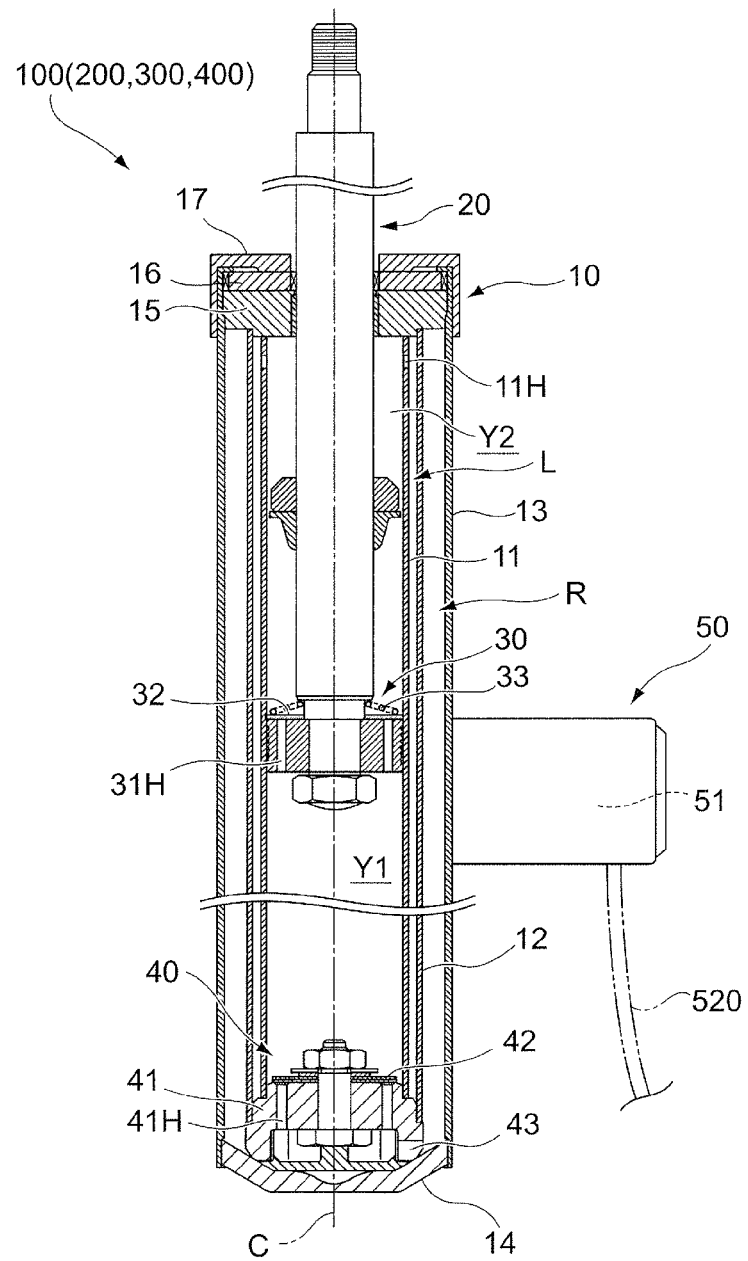
FIG. 2 is a vertical cross-sectional view showing the damper shown in FIG. 1.

FIG. 2 is a vertical cross-sectional view showing the damper 100 (200, 300, 400) shown in FIG. 1. The damper 100 shown in FIG. 2 is provided with a cylinder portion 10, a piston rod 20, a piston 30, a bottom valve 40, and a damping force variable mechanism 50.

(Schematic Configuration)

The cylinder portion 10 has a so-called triple-tube structure provided with a cylinder 11, an outer cylinder 12, and a damper case 13 successively arranged from an inside in a radial direction about an axis C, and contains oil (an example of hydraulic oil). The bottom part of the cylinder portion 10 is sealed by a bottom cover 14, and the upper part thereof is sealed by a rod guide 15, an oil seal 16, and a cap 17 so as to allow the piston rod 20 to pass through.

The piston rod 20 is movable along the direction of the axis C with some part thereof put inside a rod chamber Y2 of the cylinder portion 10 and the other part thereof exposed to the outside of the cylinder portion 10.

The piston 30 is fixed to the lower end of the piston rod 20 in FIG. 2 and movable in the direction of the axis C integrally with the piston rod 20. The piston 30 is provided so as to be movable in the direction of the axis C along the inner peripheral surface of the cylinder 11. The piston 30 is provided with a check valve 32 that opens/closes a flow path 31H and is pressed by a spring 33, and partitions space inside the cylinder 11 into the rod chamber Y2 and a piston chamber Y1. The bottom valve 40 is provided with a valve body 41 having a plurality of flow paths 41H and a damping valve 42 that opens/closes a flow path 41H provided on the side of the piston chamber Y1.

Between the cylinder 11 and the outer cylinder 12, a communication path L is formed. Near the upper end of the cylinder 11, a cylinder opening 11H that allows the rod chamber Y2 and the communication path L to communicate with each other is formed. Between the outer cylinder 12 and the damper case 13, a reservoir chamber R is formed. The piston chamber Y1 and the reservoir chamber R communicate with each other via the flow paths 41H formed in the valve body 41 of the bottom valve 40 and a concave portion 43.

(Damping Force Variable Mechanism 50)

The damping force variable mechanism 50 is provided outside the damper case 13. The damping force variable mechanism 50 is provided with a solenoid valve 51, which varies a throttling amount with an excitation force generated according to a size of an input current (an example of a signal), on the flow path of oil from the communication path L to the reservoir chamber R. Further, by changing the throttling amount with the solenoid valve 51, the damping force variable mechanism 50 changes a damping force of the damper 100.

The solenoid valve 51 is provided with a coil to be energized, a fixed core to be excited by the coil that has generated a magnetic field through energization, a magnetic body to be attracted by the excited fixed core, a valve body to be moved integrally with the magnetic body, or the like, each of which is not shown in FIG. 2.

Further, a change in the throttling amount with the solenoid valve 51 is realized in such a way that a size of a current flowing through the coil is changed.

The solenoid valve 51 is connected to a harness 520 connected to a controller 510 (see FIG. 1) of the vehicle 500, and the controller 510 causes a current to flow through the solenoid valve 51 via the harness 520.

When a relatively large current is input to the solenoid valve 51, the throttling amount becomes large, whereby a relatively high damping force is generated by the damping force variable mechanism 50. On the other hand, when a relatively small current is input to the solenoid valve 51, the throttling amount becomes small, whereby a relatively low damping force is generated by the damping force variable mechanism 50.

Note that when no current is input to the solenoid valve 51, the valve body that changes the throttling amount is movable while being free from an excitation force. Accordingly, when no current is input, the valve body is moved by oil passing through a throttle.

(Operations of Dampers 100, 200, 300, and 400)
(Operation in Compression Stroke)

Next, the operation of the damper 100 (200, 300, 400) having the above configuration will be described.

First, an operation in the compression stroke of the damper 100 will be described. In the compression stroke, pressure inside the piston chamber Y1 increases when the piston 30 moves downward in the direction of the axis C of FIG. 2. At this time, the damping valve 42 of the bottom valve 40 is in a state of closing the flow path 41H.

On the other hand, the check valve 32 of the piston 30 opens the flow path 31H. Then, oil flows from the piston chamber Y1 into the rod chamber Y2. In addition, oil corresponding to a volume of the piston rod 20 putting in the rod chamber Y2 flows out from the cylinder opening 11H into the communication path L, and the flowing-out oil flows from the communication path L into the damping force variable mechanism 50.

The oil flowing into the damping force variable mechanism 50 flows into the reservoir chamber R via the throttle varied by the solenoid valve 51. At this time, a damping force is generated in the compression stroke.

(Operation in Extension Stroke)

Next, an operation in the extension stroke of the damper 100 will be described. When the piston 30 moves upward in the direction of the axis C of FIG. 2, pressure inside the piston chamber Y1 becomes negative. Thus, oil inside the reservoir chamber R successively passes through the concave portion 43 and the flow paths 41H of the bottom valve 40 and opens the damping valve 42 to flow into the piston chamber Y1.

In addition, pressure inside the rod chamber Y2 increases with the upward movement of the piston 30 in the direction of the axis C. Thus, oil inside the rod chamber Y2 flows out from the cylinder opening 11H into the communication path L, and the flowing-out oil flows from the communication path L into the damping force variable mechanism 50.

The oil flowing into the damping force variable mechanism 50 flows into the reservoir chamber R via the throttle varied by the solenoid valve 51. At this time, a damping force is generated in the compression stroke.

(Characteristics of Damping Force by Damping Force Variable Mechanism 50)

Here, a change in the characteristics of a damping force by the damping force variable mechanism 50 will be described.

Figure 3:
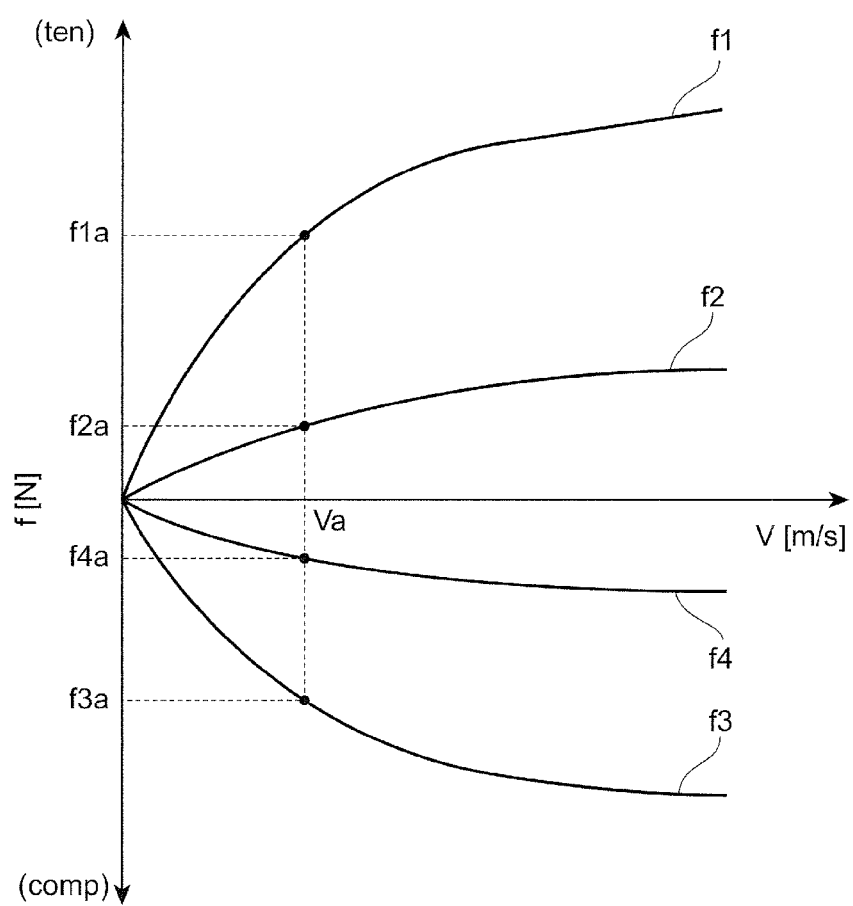
FIG. 3 is a diagram showing an example of the characteristic curves of a damping force in the extension stroke and the compression stroke of the damper switched by the damping force variable mechanism shown in FIG. 2.

FIG. 3 is a diagram showing an example of the characteristic curves of a damping force fin the extension stroke and the compression stroke of the damper 100. Each of characteristic curves f1 and f3 in FIG. 3 is a characteristic curve obtained when the damper 100 generates a relatively high damping force (hereinafter simply called a high damping force) in the extension stroke (ten side) and the compression stroke (comp side) with the input of a high current (for example, a current of 0.8 (A)) to the solenoid valve 51 (see FIG. 2).

On the other hand, each of characteristic curves f2 and f4 in FIG. 3 is a characteristic curve obtained when the damper 100 generates a relatively low damping force (hereinafter simply called a low damping force) in the extension stroke and the compression stroke with the input of a low current (for example, a current of 0.3 (A)) to the solenoid valve 51.

Note that the characteristic curves of the damping forces shown in FIG. 3 are set in advance according to a current or the like fed to the solenoid valve 51.

(Configuration of Examination System 600)

Next, the examination system 600 (see FIG. 1) for the damping force variable mechanisms 50 of the dampers 100, 200, 300, and 400 of the first embodiment will be described.

The damping force variable mechanism 50 of each of the dampers 100, 200, 300, and 400 described above changes a level of a damping force. However, there is a likelihood that the movement of the valve body of the solenoid valve 51 is not allowed, for example, when the solenoid valve 51 (see FIG. 2) is clogged with dust or the like generated in oil. In this case, the damping force variable mechanism 50 is not allowed to change a damping force.

The examination system 600 of the first embodiment is a system that examines whether the damping force variable mechanism 50 normally operates.

The examination system 600 for the damping force variable mechanisms 50 of the first embodiment is provided with a detection device 2 (see FIG. 1) that detects an output from the vehicle 500 when the dampers 100, 200, 300, and 400 are operated in a state in which the dampers 100, 200, 300, and 400, each of which is provided with the damping force variable mechanism 50 that changes a damping force according to an input current (an example of a signal), are installed in the vehicle 500.

Here, when "the dampers 100, 200, 300, and 400 are operated," the "dampers 100, 200, 300, and 400 are compressed or extended."

In addition, as a method for "operating the dampers 100, 200, 300, and 400 in a state in which the dampers 100, 200, 300, and 400 are installed in the vehicle 500," a load may be imposed on the vehicle 500 to operate the vehicle 500 or the vehicle 500 is caused to run and get over a step to be moved.

Figure 4A:
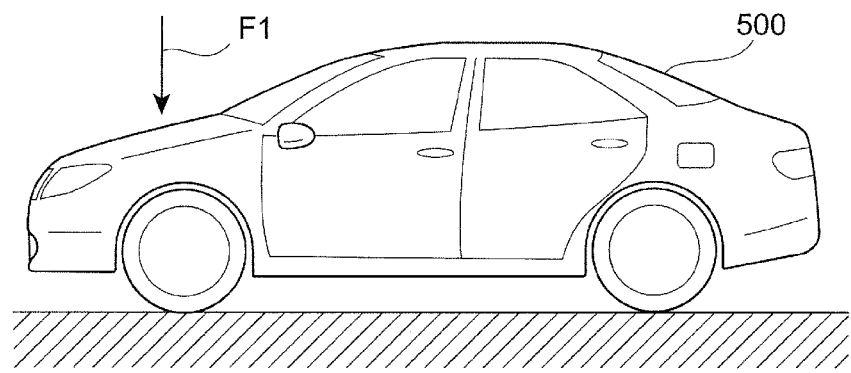
FIGS. 4A to 4C are views showing an example of imposing a load on a vehicle, FIG. 4A showing a method for causing a vertical load to act on the vehicle, FIG. 4B showing a method for causing a load in a vehicle-width direction to act on the vehicle, FIG. 4C showing a method for raising the vehicle once and then lowering (imposing a load, i.e., gravity on) the same.

FIG. 4A is a view showing an example of a method for imposing a load on the vehicle 500 in which a load F1 in a vertical direction (hereinafter called a vertical load F1) is caused to act on the vehicle 500 to operate the dampers 100, 200, 300, and 400 (see FIG. 1).

Note that the step of operating the dampers 100, 200, 300, and 400 corresponds to an example of an operation step in the examination method of the present invention.

(Detection Device 2)

The vehicle 500 (see FIG. 1) in which the dampers 100, 200, 300, and 400 as examination targets are installed is provided with the harness 520 for the vehicle 500 that connects the controller 510 and the damping force variable mechanisms 50 to each other. The harness 520 is provided with a main harness 521 connected to the controller 510 and an examination harness 522 used to connect the detection device 2.

The main harness 521 is connected to the controller 510 at all times, and the examination harness 522 is connected to the detection device 2 only when the examination system 600 of the first embodiment performs an examination.

Note that when the harness 520 is not provided with the examination harness 522, the main harness 521 may be detached from the controller 510 and connected to the detection device 2. In addition, the main harness 521 may be connected to both the controller 510 and the detection device 2.

The detection device 2 detects, as an output from the vehicle 500, an output from each of the damping force variable mechanisms 50 of the dampers 100, 200, 300, and 400 installed in the vehicle 500. Specifically, the detection device 2 determines that the damping force variable mechanism 50 is normal when the solenoid valve 51 (see FIG. 2) normally operates, and determines that the damping force variable mechanism 50 is abnormal when the solenoid valve 51 does not normally operate.

The determination as to whether the solenoid valve 51 normally operates is performed in such a way that the detection device 2 detects an induction current generated in the solenoid valve 51.

That is, the detection device 2 detects an induction current generated in the solenoid valve 51, for example, when the vertical load F1 is caused to act on the vehicle 500 (see FIG. 1) to operate each of the dampers 100, 200, 300, and 400 in a state in which no current is fed to the solenoid valve 51 (a current of 0 (A) is fed). Then, the detection device 2 determines whether the solenoid valve 51 normally operates based on the presence or absence of the induction current.

The state in which no current is fed to the solenoid valve 51 may be realized by the control of the controller 510, or may be realized by the detachment of the controller 510 from the main harness 521.

Figure 5:
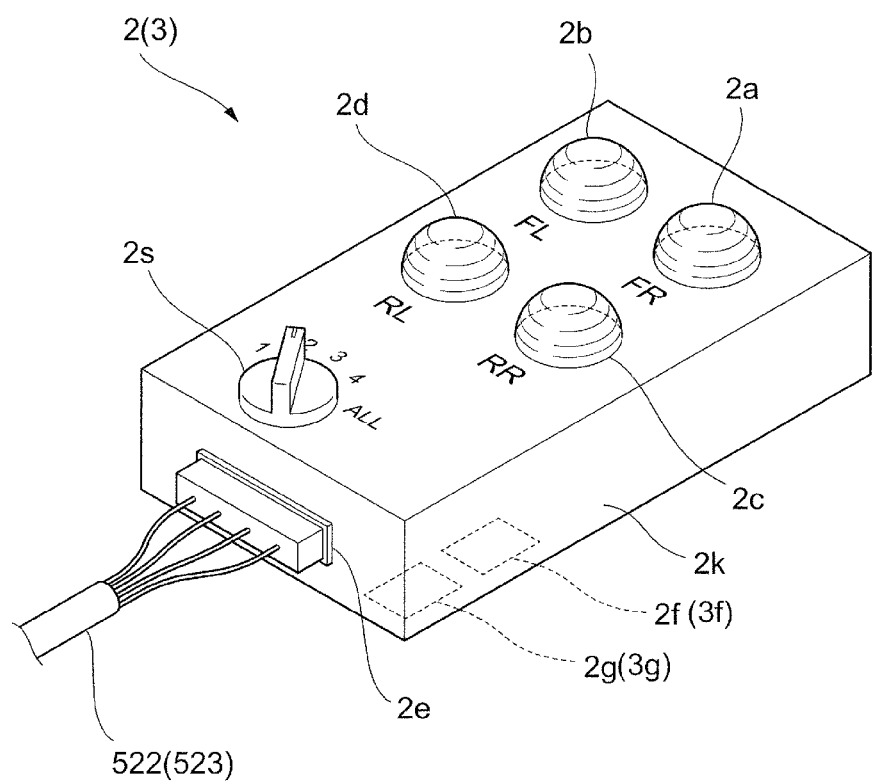
FIG. 5 is a view showing an example of a detection device (or an output device)

FIG. 5 is a view showing an example of the specific configuration of the detection device 2. The detection device 2 has a case 2k in which four lamps 2a, 2b, 2c, and 2d, a rotary switch 2s, a connection unit 2e, a storage unit 2f, and a determination unit 2g are provided.

The connection unit 2e is connected to the examination harness 522. The rotary switch 2s is a selector switch by which one damping force variable mechanism 50 as a detection target or all the damping force variable mechanisms 50 out of the four damping force variable mechanisms 50 of the four dampers 100, 200, 300, and 400 installed in the vehicle 500 (see FIG. 1) are selected.

The lamp 2a corresponds to the damper 100 (see FIG. 1) of the right front wheel of the vehicle 500. The lamp 2b corresponds to the damper 200 of the left front wheel of the vehicle 500. The lamp 2c corresponds to the damper 300 of the right rear wheel of the vehicle 500. The lamp 2d corresponds to the damper 400 of the left rear wheel of the vehicle 500. Each of the lamps 2a, 2b, 2c, and 2d emits green light.

The storage unit 2f temporarily stores an induction current when the induction current is input to the storage unit 2f from each of the dampers 100, 200, 300, and 400.

The determination unit 2g determines whether the damping force variable mechanism 50 of each of the dampers 100, 200, 300, and 400 is normal based on the presence or absence of an induction current. In addition, when it is determined that the damping force variable mechanisms 50 are normal, the determination unit 2g causes the corresponding lamps 2a, 2b, 2c, and 2d to emit green light. On the other hand, when it is not determined that the damping force variable mechanisms 50 are normal (i.e., when it is determined that the damping force variable mechanisms 50 are abnormal), the determination unit 2g does not cause the corresponding lamps 2a, 2b, 2c, and 2d to emit light.

Specifically, when the coil of a damper as an examination target (for example, the damper 100 of the right front wheel) selected by the rotary switch 2s generates an induction current by an examination, the determination unit 2g determines that the damping force variable mechanism 50 of the damper 100 is normal and causes the lamp 2a corresponding to the damper 100 of the right front wheel to emit green light.

On the other hand, when the coil of the damper 100 of the right front wheel produces no induction current by the examination, the determination unit 2g does not determine that the damping force variable mechanism 50 of the damper 100 is normal and does not cause the lamp 2a corresponding to the damper 100 of the right front wheel to emit light.

Operations for the other lamps 2b, 2c, and 2d by the determination unit 2g are the same as the operation for the lamp 2a described above.

Note that the operation by the detection device 2 corresponds to an example of a detection step in the examination method of the present invention in which a change occurring in the vehicle 500 is detected.

(Function)

The function of the examination system 600 of the first embodiment will be described.

As shown in FIG. 1, the vertical load F1 is imposed on the vehicle 500 (see FIG. 4A: details will be described later) in a state in which the examination harness 522 is connected to the detection device 2 and no current is input to the solenoid valves 51 (see FIG. 2). Thus, the vehicle 500 moves downward, and the dampers 100, 200, 300, and 400 operate in the compression stroke.

As described above, oil passes through the throttle of the damping force variable mechanism 50 in the compression stroke of the dampers 100, 200, 300, and 400. At this time, when the solenoid valve 51 normally operates, the valve body is moved to generate an induction current in the solenoid valve 51.

The induction current is detected by the detection device 2. When the induction current is detected from one of the dampers 100, 200, 300, and 400 as a detection target (or all the four dampers 100, 200, 300, and 400 as detection targets) selected by the rotary switch 2s (see FIG. 5), the detection device 2 causes a corresponding one of the lamps 2a, 2b, 2c, and 2d (or all the four lamps 2a, 2b, 2c, and 2d) to emit green light.

On the other hand, when no induction current is detected, the detection device 2 does not cause a corresponding one of the lamps 2a, 2b, 2c, and 2d (or all the four lamps) to emit light.

As described above, according to the examination system 600 for the damping force variable mechanisms 50 of the first embodiment, an examination as to whether the damping force variable mechanisms 50 are normal is allowed in a state in which the dampers 100, 200, 300, and 400 are installed in the vehicle 500.

Note that the first embodiment is not limited only to a state in which no current is input to the solenoid valves 51, but the following method is applicable.

That is, some damping force variable mechanisms 50 may have a fail-safe mode. In the fail-safe mode, the movement of the valve body stops at a moment at which the valve body attempts to move with the solenoid valve 51 not energized (see FIG. 2).

When the damping force variable mechanism 50 that shifts to the fail-safe mode when the valve body moves with the solenoid valve 51 not energized as described above is examined by the configuration of the first embodiment, it is necessary to energize the solenoid valve 51 such that the damping force variable mechanism 50 is prevented from shifting to the fail-safe mode (such that the movement of the valve body is hindered).

In view of this, when the damping force variable mechanism 50 that shifts to the fail-safe mode is examined by the configuration of the first embodiment, an extremely small current that is extremely close to 0 (A) but does not allow the damping force variable mechanism 50 to shift to the fail-safe mode may be input to the solenoid valve 51 instead of inputting a current of 0 (A) to the solenoid valve 51. In this case, the extremely small current to the solenoid valve 51 may be supplied from the detection device 2.

Note that even when the vehicle 500 is moved in a state in which the above extremely small current is fed to the solenoid valve 51, the detection of an output (induction current) from the solenoid valve 51 is allowed as in a case in which the vehicle 500 is moved with the solenoid valve 51 not energized.

The above operation of the first embodiment corresponds to an embodiment of the examination method for the damping force variable mechanism of the present invention, the examination method including: the operation step of operating the dampers 100, 200, 300, and 400; and the detection step of detecting a change occurring in the vehicle 500 due to the operation step in a state in which the dampers 100, 200, 300, and 400, each of which is provided with the damping force variable mechanism 50 that changes a damping force according to an input signal, are installed in the vehicle 500. Further, according to the examination method corresponding to the operation of the first embodiment, an examination as to whether the damping force variable mechanisms 50 are normal is allowed in a state in which the dampers 100, 200, 300, and 400 are installed in the vehicle 500.

Second Embodiment

Figure 6:
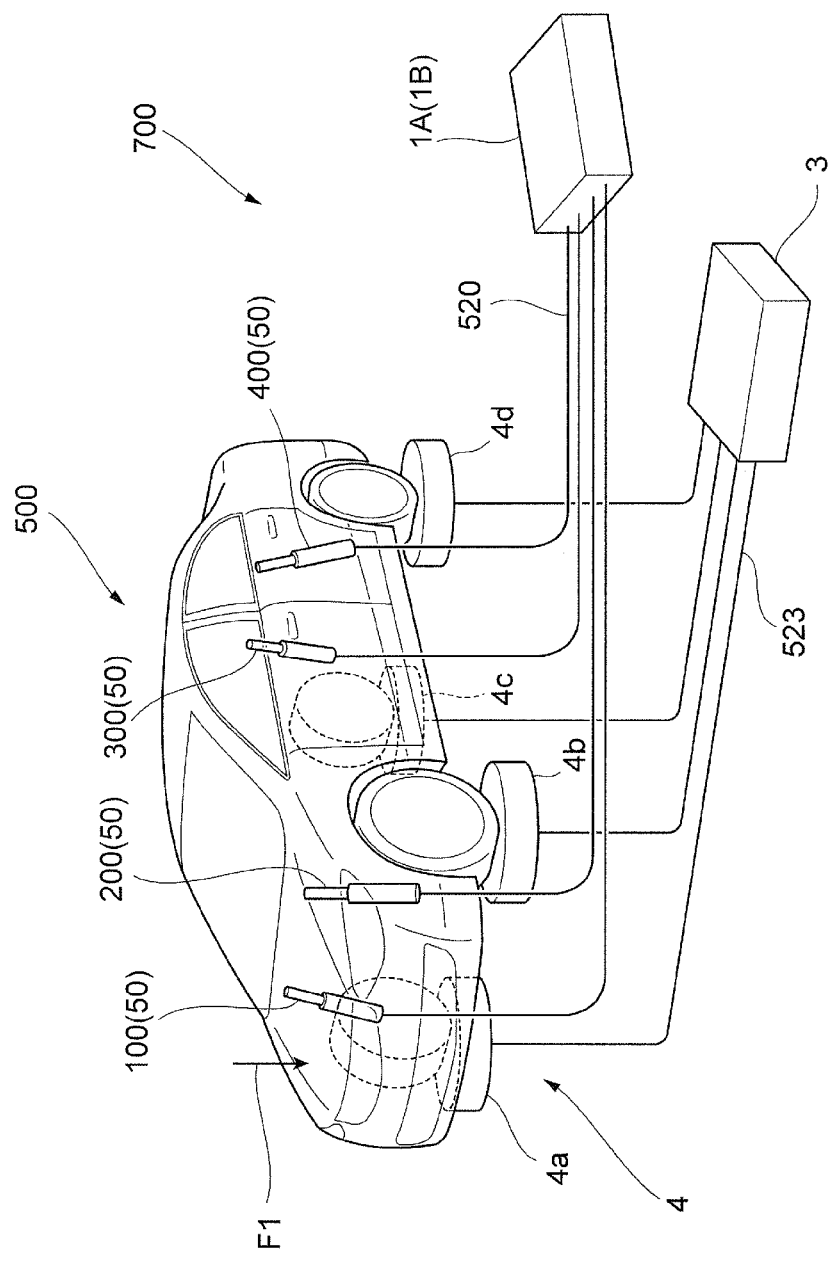
FIG. 6 is a schematic view showing an examination system for the damping force variable mechanism in the damper according to a second embodiment and a variation of the present invention.

Next, an examination system 700 according to a second embodiment of the present invention will be described. FIG. 6 is a view showing the examination system 700 for the damping force variable mechanisms 50 of the dampers 100, 200, 300, and 400 according to the second embodiment.

(Configuration)

(Configuration of Examination System 700)

The examination system 700 for the damping force variable mechanisms 50 of the second embodiment is provided with a wheel load meter 4 as an example of a detection device that detects an output from the vehicle 500 when the dampers 100, 200, 300, and 400 are operated in a state in which the dampers 100, 200, 300, and 400, each of which is provided with the damping force variable mechanism 50 that changes a damping force according to an input current (an example of a signal), are installed in the vehicle 500.

In addition, the examination system 700 for the damping force variable mechanisms 50 of the second embodiment is further provided with a signal input device 1A that inputs a current (an example of a signal) to the damping force variable mechanisms 50, and the wheel load meter 4 detects a wheel load of the vehicle 500 when the vehicle 500 is moved so as to operate the dampers 100, 200, 300, and 400 in a state in which the current is input to the damping force variable mechanisms 50 by the signal input device 1A.

Note that the step of moving the vehicle 500 so as to operate the dampers 100, 200, 300, and 400 corresponds to an example of the operation step in the examination method of the present invention.

(Signal Input Device 1A)

Here, the signal input device 1A in the examination system 700 of the second embodiment inputs a variable current as an example to the damping force variable mechanisms 50.

FIGS. 7A to 7D are diagrams each showing a current (an example of a signal), the value of which changes, the current being input to the damping force variable mechanisms 50 by the signal input device 1A.

Figure 7A:
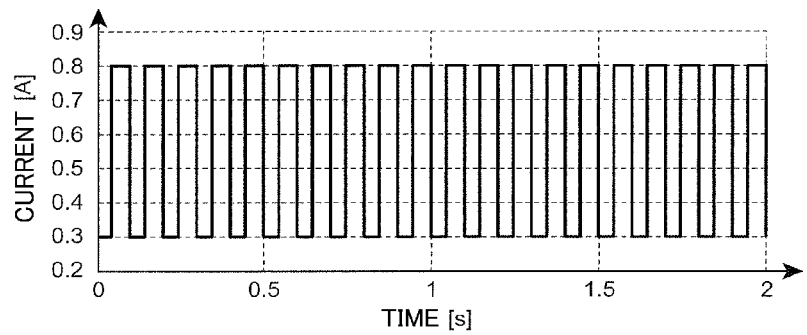
FIGS. 7A to 7D are diagrams each showing a signal having a current value that changes, the signal being input to the damping force variable mechanism, FIG. 7A showing a current that has a constant change cycle and has the same pulse width at high and low levels, FIG. 7B showing a current that has a constant change cycle, three levels of current values, i.e., high, middle, and low current values, and has the same pulse width at high, middle, and low levels, FIG. 7C showing a current that has a fluctuating change cycle, has two levels of current values, i.e., high and low current values, and has a longer pulse width at a low level than a pulse width at a high level, FIG. 7D showing a current that has a fluctuating change cycle, has three levels of current values, i.e., high, middle, and low current values, has different pulse widths at high, middle, and low levels.

FIG. 7A is a diagram showing an example of a current that changes between high and low levels, has a constant change cycle, and has the same pulse width at high and low levels. The current shown in the graph is a current that alternately changes between a high current (for example, a current of 0.8 (A)) at which the dampers 100, 200, 300, and 400 show the characteristic curves f1 and f3 (see FIG. 3) of a high damping force and a low current (for example, a current of 0.3 (A)) at which the dampers 100, 200, 300, and 400 show the characteristic curves f2 and f4 of a low damping force.

In addition, as shown in FIG. 7A, the signal input device 1A in the second embodiment is set such that the cycle of a change in the level of the current input to the damping force variable mechanism 50 is made constant. Here, the constant cycle of the change in the level of the current is set at, for example, 10 (Hz).

Note that a size (current value), a cycle, a waveform, and the like of the signal are not limited to those shown in FIG. 7A. For example, the waveform of the signal may include various waves such as a triangular wave and a saw-tooth wave besides a rectangular wave.

Figure 7B:
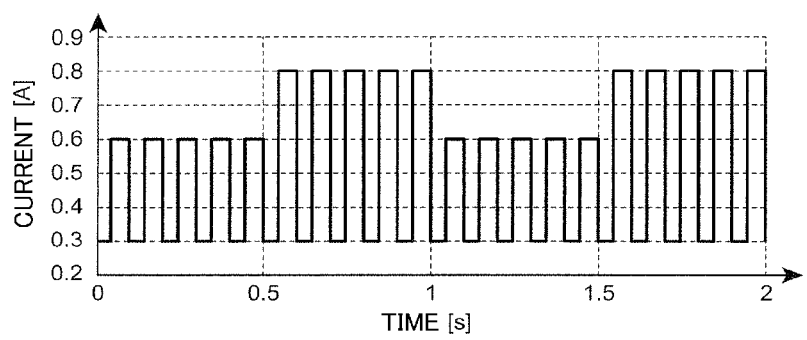

FIG. 7B is a diagram showing an example of a current that has a constant change cycle, has three levels of current values, i.e., high, middle, and low current values, and has the same pulse width at high, middle, and low levels. Specifically, in FIG. 7B, three mutually different currents are switched to each other. In this example, a low current (for example, a current of 0.3 (A)) is shared as a low-side current, and a high current (for example, a current of 0.8 (A)) and a middle current (for example, a current of 0.6 (A)) are switched to each other as high-side currents, and the current is oscillated between the low-side current and the high-side current.

Further, the current shown in FIG. 7B may be input to the damping force variable mechanisms 50. Note that in FIG. 7B, the middle current and the high current are switched to each other as high-side currents. Besides, currents of three different sizes may be applied as high-side currents, or currents of four or more different sizes may be applied.

Similarly, currents of two or more different sizes may be applied as low-side currents.

Figure 7C:
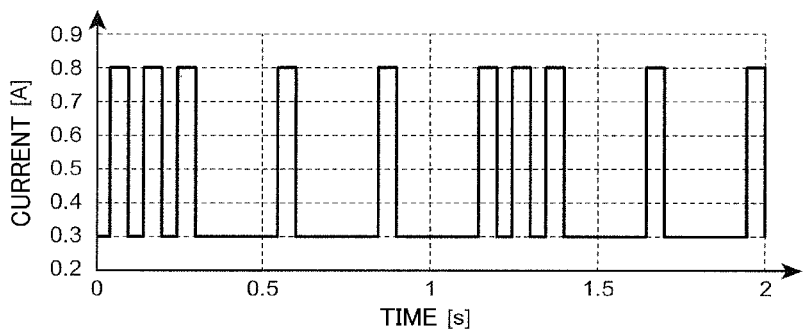

FIG. 7C is a diagram showing an example of a current that has a fluctuating change cycle, has two levels of current values, i.e., high and low current values, and has a longer pulse width at a low level than a pulse width at a high level. Such a current may be input to the damping force variable mechanisms 50.

Note that the current shown in FIG. 7C is a current that changes at two types of frequencies. Besides, a current that changes at three frequencies may be applied, or a current that changes at four or more frequencies may be applied.

In addition, a pulse width of a low current may be the same as that of a high current, or a pulse width of a high current may be longer than that of a low current.

Figure 7D:
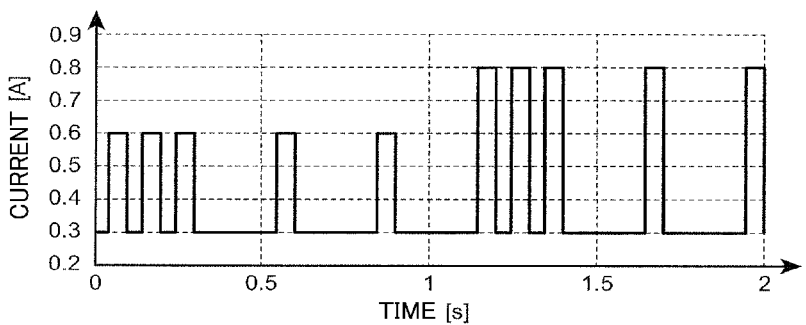

FIG. 7D is a diagram showing an example of a current that has a fluctuating change cycle, has three levels of current values, i.e., high, middle, and low current values, partially has different pulse widths at high, middle, and low levels. Such a current may be input to the damping force variable mechanisms 50.

Note that the current shown in FIG. 7D is a current that changes at two types of frequencies. Besides, a current that changes at three frequencies may be applied, or a current that changes at four or more frequencies may be applied.

As the waveforms of the currents shown in FIGS. 7A to 7D, various waveforms such as a triangular wave and a saw-tooth wave besides the illustrated rectangular wave may be applied.

Further, as shown in FIG. 6, the signal input device 1A is connected to the harness 520 instead of the controller 510 (see FIG. 1). Thus, the signal input device 1A is connected to the damping force variable mechanisms 50. Note that both the signal input device 1A and the controller 510 may be connected to the harness 520. In the second embodiment, the harness 520 is not provided with the examination harness 522 shown in FIG. 1.

Provided that the controller 510 (see FIG. 1) provided in advance in the vehicle 500 is capable of outputting a variable current and is output from the signal input device 1A of the second embodiment, the controller 510 may be used instead of the signal input device 1A. In this case, the controller 510 corresponds to an example of a signal input device in the present invention.

(Detection Device: Wheel Load Meter 4)

In the second embodiment, the wheel load meter 4 that detects a wheel load of each of the wheels of the vehicle 500 is applied as an example of the detection device in the present invention. That is, a wheel load of the vehicle 500 is an example of an output from the vehicle in the present invention.

The wheel load meter 4 is provided with wheel load detection units 4a, 4b, 4c, and 4d, each of which is arranged beneath each of the wheels of the vehicle 500 and detects a weight of a corresponding one of wheels. In addition, the wheel load meter 4 is provided with an output device 3 that outputs the presence or absence of a change in the wheel load based on the wheel load detected by each of the wheel load detection units 4a, 4b, 4c, and 4d, and provided with a harness 523 that connects each of the wheel load detection units 4a, 4b, 4c, and 4d and the output device 3 to each other.

The output device 3 may have the same configuration as that of the detection device 2 (see FIG. 5) of the first embodiment.

The operation of the wheel load meter 4 corresponds to an example of the detection step of detecting a change in the wheel load occurring in the vehicle 500.

(Function)

Next, the function of the examination system 700 of the second embodiment will be described.

As shown in FIG. 6, in the examination system 700, each of the wheels of the vehicle 500 is in a state of being placed on a corresponding one of the wheel load detection units 4a, 4b, 4c, and 4d. In this state, a current that changes between high and low levels at a constant cycle of 10 (Hz) (see FIG. 7A) is input from the signal input device 1A to the damping force variable mechanism 50 of each of the dampers 100, 200, 300, and 400. Then, the vertical load F1 is input to the vehicle 500 while the current is input. The input of the vertical load F1 to the vehicle 500 is performed in the same way as that of the first embodiment.

A damping force that may be generated by each of the dampers 100, 200, 300, and 400 with the input of the current from the signal input device 1A is switched between the high damping force of the characteristic curve f3 and the low damping force of the characteristic curve f4 shown in FIG. 3 according to the cycle of the change in the level of the current.

In this period, when the vertical load F1 is imposed on the vehicle 500 such that the dampers 100, 200, 300, and 400 are operated at a speed of Va (m/s), the damping force generated by each of the dampers 100, 200, 300, and 400 changes between a high damping force f3a (N) and a low damping force f4a (N) shown in FIG. 3 at a constant cycle of 10 (Hz).

As a result, each of the wheel load detection units 4a, 4b, 4c, and 4d detects the wheel load changing at a constant cycle of 10 (Hz) according to the change in the damping force generated by each of the dampers 100, 200, 300, and 400. The wheel load detected by each of the wheel load detection units 4a, 4b, 4c, and 4d is input to the output device 3 and stored in a storage unit 3f (see FIG. 5).

On the other hand, when the damping force variable mechanism 50 of each of the dampers 100, 200, 300, and 400 does not normally operate, the damping force that may be generated by each of the dampers 100, 200, 300, and 400 does not change. Accordingly, the wheel load detected by each of the wheel load detection units 4a, 4b, 4c, and 4d does not change at a constant cycle of 10 (Hz). The wheel load detected by each of the wheel load detection units 4a, 4b, 4c, and 4d is input to the output device 3 and stored in the storage unit 3f (see FIG. 5).

A determination unit 3g of the output device 3 causes each of the lamps 2a, 2b, 2c, and 2d to emit light according to whether the wheel load input from each of the wheel load detection units 4a, 4b, 4c, and 4d and stored in the storage unit 3f has changed corresponding to the change in the current input to the damping force variable mechanism 50.

Specifically, when the wheel load input from each of the wheel load detection units 4a, 4b, 4c, and 4d and stored in the storage unit 3f has changed at a cycle of 10 (Hz) the same as that of the change in the current input to the damping force variable mechanism 50, the determination unit 3g determines that the damping force variable mechanisms 50 of the dampers 100, 200, 300, and 400 corresponding to the wheel load detection units 4a, 4b, 4c, and 4d normally operate. Then, the determination unit 3g causes the lamps 2a, 2b, 2c, and 2d to emit green light.

On the other hand, when the wheel load input from each of the wheel load detection units 4a, 4b, 4c, and 4d and stored in the storage unit 3f has not changed at a cycle of 10 (Hz) the same as that of the change in the current input to the damping force variable mechanism 50, the determination unit 3g does not determine that the damping force variable mechanisms 50 of the dampers 100, 200, 300, and 400 corresponding to the wheel load detection units 4a, 4b, 4c, and 4d normally operate. Then, the determination unit 3g does not cause the lamps 2a, 2b, 2c, and 2d to emit light.

As described above, according to the examination system 700 for the damping force variable mechanisms 50 of the second embodiment, the damping force variable mechanisms 50 can be examined in a state in which the dampers 100, 200, 300, and 400 are installed in the vehicle 500.

In the second embodiment, the signal input device 1A produces the constant cycle of the change in the level of the current input to each of the damping force variable mechanisms 50. Therefore, detection by the output device 3 is facilitated.

Further, as a reason why the damping force variable mechanism 50 does not normally operate, the restricted movement of the valve body due, for example, to the clogging of the solenoid valve 51 with dust generated in oil is assumed.

In such a case, according to the examination system 700 of the second embodiment, the removal of clogged dust is expectable in such a way that a current changing between high and low levels is input by the signal input device 1A to the solenoid valve 51 to slightly vibrate the valve body.

Note that the cycle of the change in the level of the current input to each of the wheel load detection unit 4a, 4b, 4c, and 4d may be stored in advance in the output device 3, or the output device 3 may detect the cycle when the current input from the signal input device 1A to each of the wheel load detection units 4a, 4b, 4c, and 4d is partially input to the output device 3.

In addition, the operation of the second embodiment includes: the operation step of operating the dampers 100, 200, 300, and 400 in a state in which the dampers 100, 200, 300, and 400, each of which is provided with the damping force variable mechanism 50 that changes a damping force according to an input signal, are installed in the vehicle 500; and the detection step of detecting a wheel load as a change occurring in the vehicle 500 due to the operation step. Further, in the operation step, the dampers 100, 200, 300, and 400 are operated in a state in which a variable signal is input to the damping force variable mechanisms 50 by the signal input device 1A. Accordingly, the operation of the second embodiment corresponds to an embodiment of the examination method for the damping force variable mechanism of the present invention.

Further, according to the examination method corresponding to the operation of the second embodiment, an examination as to whether the damping force variable mechanisms 50 are normal is allowed in a state in which the dampers 100, 200, 300, and 400 are installed in the vehicle 500.

OTHER EMBODIMENTS (Variation in Method for Imposing Load on Vehicle (Operation Step))

The first and second embodiments describe a mode in which the vertical load F1 is caused to act on the vehicle 500 (see FIGS. 1 and 6) to move the vehicle 500 to operate the dampers 100, 200, 300, and 400, but the present invention is not limited to the mode in which a vehicle is moved according to the method. That is, as a method for moving a vehicle, the present invention may employ the following mode.

(Description of Mode in which Load is Imposed on Vehicle in Stopped State)

Figure 4B:
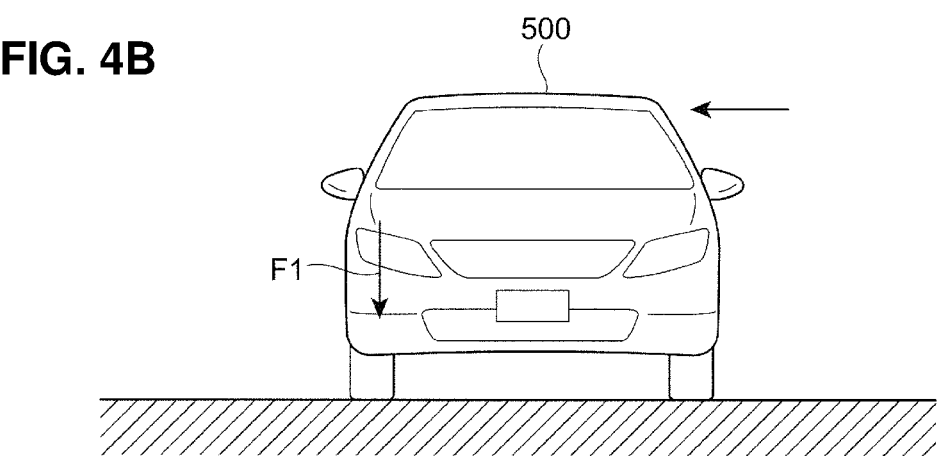
Figure 4C:
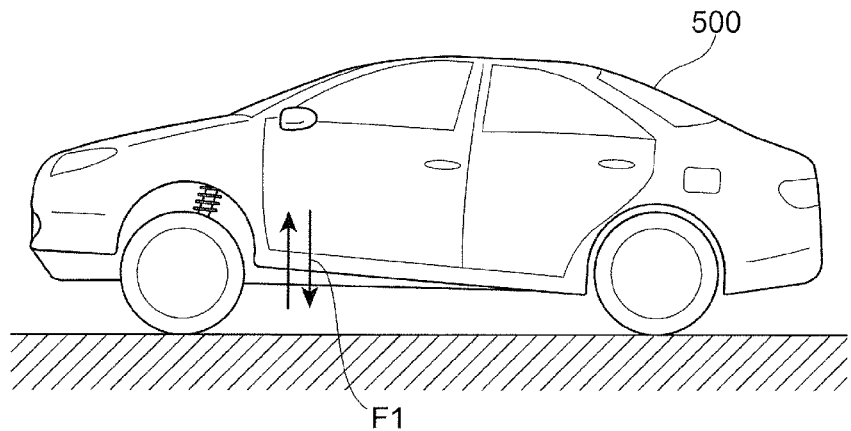

FIGS. 4B and 4C are views showing other modes of a method for imposing the vertical load F1 on the vehicle 500.

Here, a load other than the vertical load F1 may be imposed on the vehicle 500. In short, any load that extends/compresses the dampers 100, 200, 300, and 400 (see FIG. 6) may be imposed.

FIG. 4B shows a method for moving the vehicle 500 in which a load in a vehicle-width direction is caused to act on the vehicle 500 so as to make the vehicle 500 roll (rotate the vehicle 500 about an axis in the back and forth direction of the vehicle 500) to impose the vertical load F1 on the vehicle 500 to move the same. FIG. 4C shows a method for moving the vehicle 500 in which the vehicle 500 is raised once and then lowered (the vertical load F1, i.e., the gravity is imposed on the vehicle 500).

Under these modes, it is also possible to obtain the functions and effects of the first and second embodiments as in a case in which the vertical load F1 is caused to act on the vehicle 500.

Note that as a method for imposing the vertical load F1 on the vehicle 500 to move the same, an examiner or the like may perform an operation by hand or a vehicle load input mechanism as mechanical equipment may perform the operation.

Figure 8A:
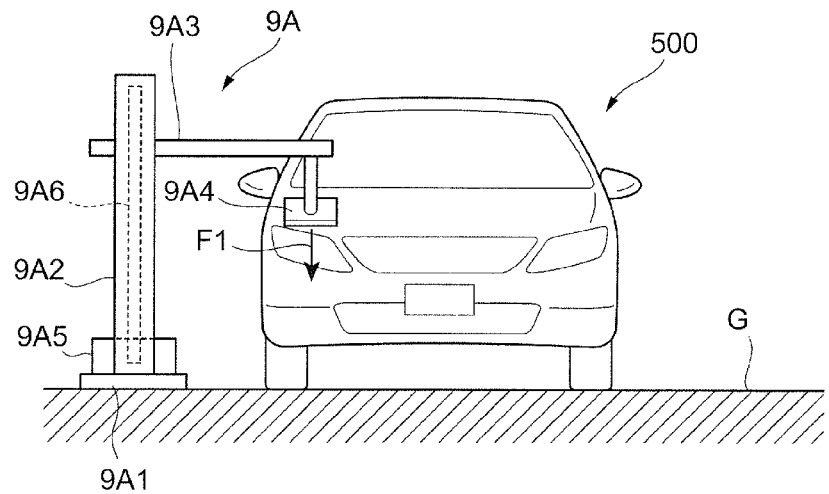
FIGS. 8A to 8C are schematic views each illustrating a vehicle load input mechanism, FIG. 8A showing a vehicle load input mechanism that causes a vertical load to act on the vehicle, FIG. 8B showing a vehicle load input mechanism that causes a load to act in the vehicle-width direction so as to make the vehicle roll, FIG. 8C showing a vehicle load input mechanism such as a hydraulic jack that raises the vehicle once and then lowers the same.
Figure 8B:
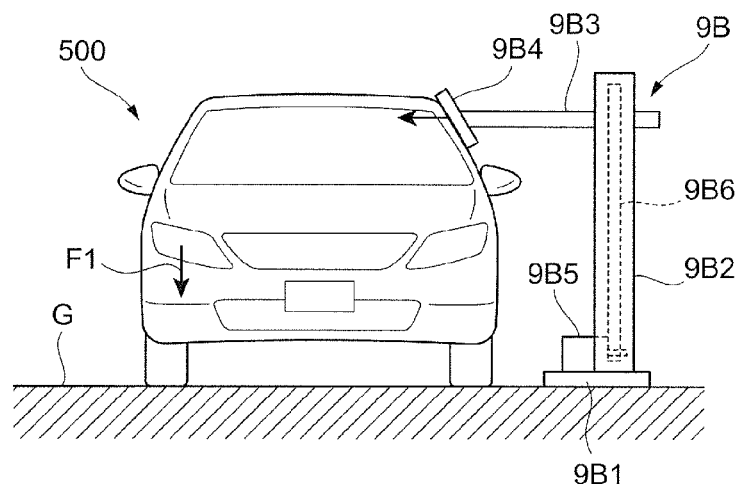
Figure 8C:
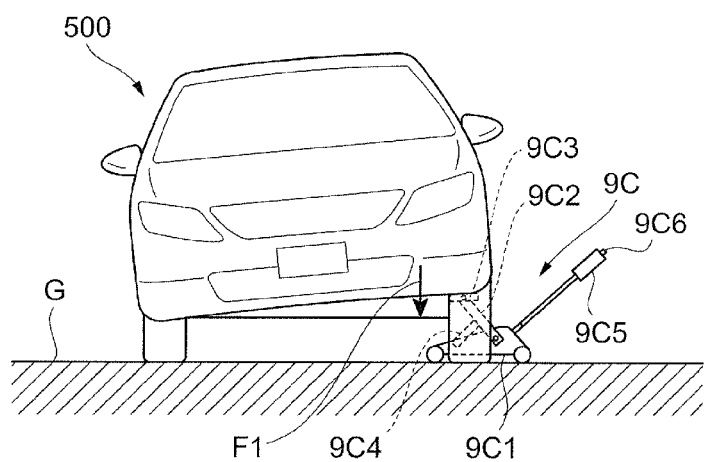

FIGS. 8A, 8B, and 8C are schematic views respectively illustrating vehicle load input mechanisms 9A, 9B, and 9C as modes of vehicle load input mechanisms used to impose the vertical load F1 on the vehicle 500 to move the same. As shown in FIGS. 8A, 8B, and 8C, the examination systems 600 and 700 for the damping force variable mechanisms 50 of the first and second embodiments may be further provided with the vehicle load input mechanisms 9A, 9B, and 9C that move the vehicle 500 so as to operate the dampers 100, 200, 300, and 400.

(First Vehicle Load Input Mechanism: See FIG. 8A)

FIG. 8A is a view showing the vehicle load input mechanism 9A that causes the vertical load F1 to act on the vehicle 500 and corresponds to the method for inputting the load (the operation step) in FIG. 4A. The vehicle load input mechanism 9A shown in FIG. 8A is provided with a base portion 9A1 that contacts a ground surface G, a support portion 9A2 that extends in a vertical direction from the base portion 9A1, an arm portion 9A3 that extends in a direction crossing the support portion 9A2 while being supported by the support portion 9A2 and is capable of performing up-and-down movements along the support portion 9A2, and a press portion 9A4 that extends vertically downward from the arm portion 9A3 and transmits the movements of the arm portion 9A3. In addition, the vehicle load input mechanism 9A is provided with a motor 9A5 provided on the base portion 9A1 and a transmission member 9A6 that converts the rotation of the motor 9A5 into up-and-down movements to cause the arm portion 9A3 to perform up-and-down movements along the support portion 9A2.

As shown in FIG. 8A, the vehicle load input mechanism 9A drives the motor 9A5 in a state in which the vehicle 500 is arranged under the press portion 9A4 and moves the press portion 9A4 downward via the transmission member 9A6 and the arm portion 9A3 to input the vertical load F1 in the vertical direction from the press portion 9A4 to the vehicle 500.

(Second Vehicle Load Input Mechanism: See FIG. 8B)

FIG. 8B is a view showing the vehicle load input mechanism 9B that causes a load in the vehicle-width direction to act on the vehicle 500 so as to make the vehicle 500 roll to input the vertical load F1 to the vehicle 500 and corresponds to the method for inputting the load (the operation step) in FIG. 4B. The vehicle load input mechanism 9B shown in FIG. 8B is provided with a base portion 9B1 that contacts the ground surface G, a support portion 9B2 that extends in a vertical direction from the base portion 9B1, an arm portion 9B3 that extends in a direction crossing the support portion 9B2 while being supported by the support portion 9B2 and is capable of moving along its extending direction, and a press portion 9B4 that transmits the movement of the arm portion 9B3. In addition, the vehicle load input mechanism 9B is provided with a motor 9B5 provided on the base portion 9B1 and a transmission member 9B6 that converts the rotation of the motor 9B5 into a movement in the extending direction of the arm portion 9B3 to cause the arm portion 9B3 to move along the support portion 9B2.

As shown in FIG. 8B, the vehicle load input mechanism 9B drives the motor 9B5 in a state in which the vehicle 500 is arranged on the lateral side of the press portion 9B4 and moves the press portion 9B4 laterally via the transmission portion 9B6 and the arm portion 9B3. Thus, the press portion 9B4 inputs a load in the vehicle-width direction to the vehicle 500 so as to make the vehicle 500 roll to input the vertical load F1.

(Third Vehicle Load Input Mechanism: See FIG. 8C)

FIG. 8C is a view showing the vehicle load input mechanism 9C such as a hydraulic jack that raises the vehicle 500 once and then lowers the same and corresponds to the method for inputting the load (the operation step) in FIG. 4C. The vehicle load input mechanism 9C shown in FIG. 8C is an elevating device that raises and lowers the vehicle 500. The elevating device is a hydraulic jack (hereinafter also called a hydraulic jack 9C) as an example.

The hydraulic jack 9C is provided with a base body 9C1 placed on the ground surface G, an arm portion 9C2 rotatably supported with respect to the base body 9C1, an elevating portion 9C3 provided at the tip end of the arm portion 9C2, a hydraulic cylinder 9C4 that is arranged between the base body 9C1 and the arm portion 9C2 and expands/contracts with hydraulic pressure to rotate the arm portion 9C2 with respect to the base body 9C1, an operation rod 9C5 to which an up-and-down movement operation for imposing hydraulic pressure on the hydraulic cylinder 9C4 to expand the hydraulic cylinder 9C4 is input, and a release button 9C6 with which an operation for releasing the hydraulic pressure of the hydraulic cylinder 9C4 is input.

As shown in FIG. 8C, the hydraulic jack 9C is arranged between the vehicle 500 and the ground surface G in a state in which the hydraulic cylinder 9C4 is contracted and the arm portion 9C2 is folded horizontally. Here, by the up-and-down movement operation of the operation rod 9C5, hydraulic pressure is imposed on the hydraulic cylinder 9C4 to expand the same. With the expansion of the hydraulic cylinder 9C4, the arm portion 9C2 rotates and rises with respect to the base body 9C1. As the rising of the arm portion 9C2 advances, the elevating portion 9C3 contacts part of the vehicle 500 and raises the vehicle 500.

When the release button 9C6 is operated in a state in which the vehicle 500 is raised as shown in FIG. 8C, hydraulic pressure inside the hydraulic cylinder 9C4 rapidly decreases. Thus, the arm portion 9C2 on which a weight of the vehicle 500 acts via the elevating portion 9C3 loses its support force directed upward by the hydraulic cylinder 9C4 and rapidly lowers.

As described above, the hydraulic jack 9C raises the vehicle 500 once and then lowers the same to input the vertical load F1 to the vehicle 500.

Figure 9:
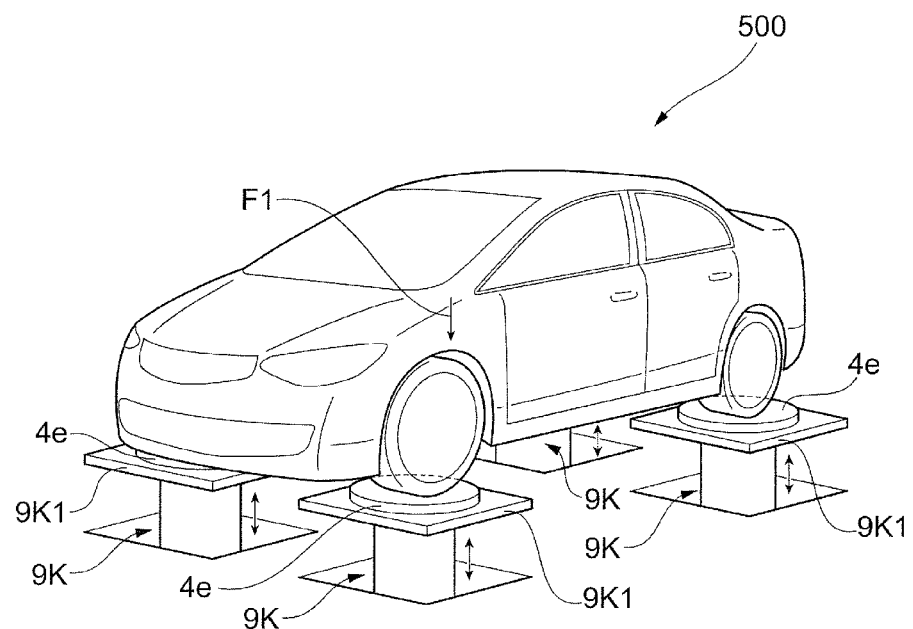
FIG. 9 is a view showing an example of applying so-called oscillation machines as elevating devices that raises and lowers the vehicle.

FIG. 9 is a view showing an example of applying so-called oscillation machines 9K as elevating devices that raises and lowers the vehicle 500. The oscillation machines 9K raise the vehicle 500 once and then lower the same to realize the operation step of inputting the vertical load F1 to the vehicle 500 to move the same.

In the oscillation machines 9K shown in FIG. 9, wheel load meters 4e are installed between the respective wheels of the vehicle 500 and support portions 9K1 of the oscillation machines 9K corresponding to the respective wheels. The dampers 100, 200, 300, and 400 (see FIG. 6) are operated by the oscillation machines 9K, and wheel loads of the respective wheels are detected by the wheel load meters 4e. Note that although the wheel load meters 4e are applied as detection devices in this example, other detection devices may be applied.

Note that the oscillation machines 9K shown in FIG. 9 are such that each of the support portions 9K1 raises and lowers each of the wheels of the vehicle 500 while separately supporting the same. Besides, a support portion configured to raise and lower two wheels while integrally supporting the same or a support portion configured to raise and lower the four wheels while integrally supporting the same may be applied.

In addition, in the operation of oscillating the vehicle 500, it is only necessary to operate (for example, extend/compress) the damper 100 as an examination target (or the other dampers 200, 300, and 400). Therefore, for example, an examiner may vertically horizontally press a place near a portion of the vehicle 500 at which the damper 100 as an examination target is installed (the operation of inputting the vertical load F1).

(Mode in which Load is Imposed on Vehicle in Running State)

(Variation 1: Input Load to Vehicle in Running State)

In the examination system and the examination method of each of the embodiments described above, the mode of the operation step in which the vehicle 500 is moved to operate the dampers 100, 200, 300, and 400 is not limited to the above method for causing the vertical load F1 to act on the vehicle 500 in a stopped state. That is, the present invention may cause a load to act on a vehicle in a running state.

Hereinafter, a mode in which a load is caused to act on a vehicle in a running state will be described.

Figure 10:
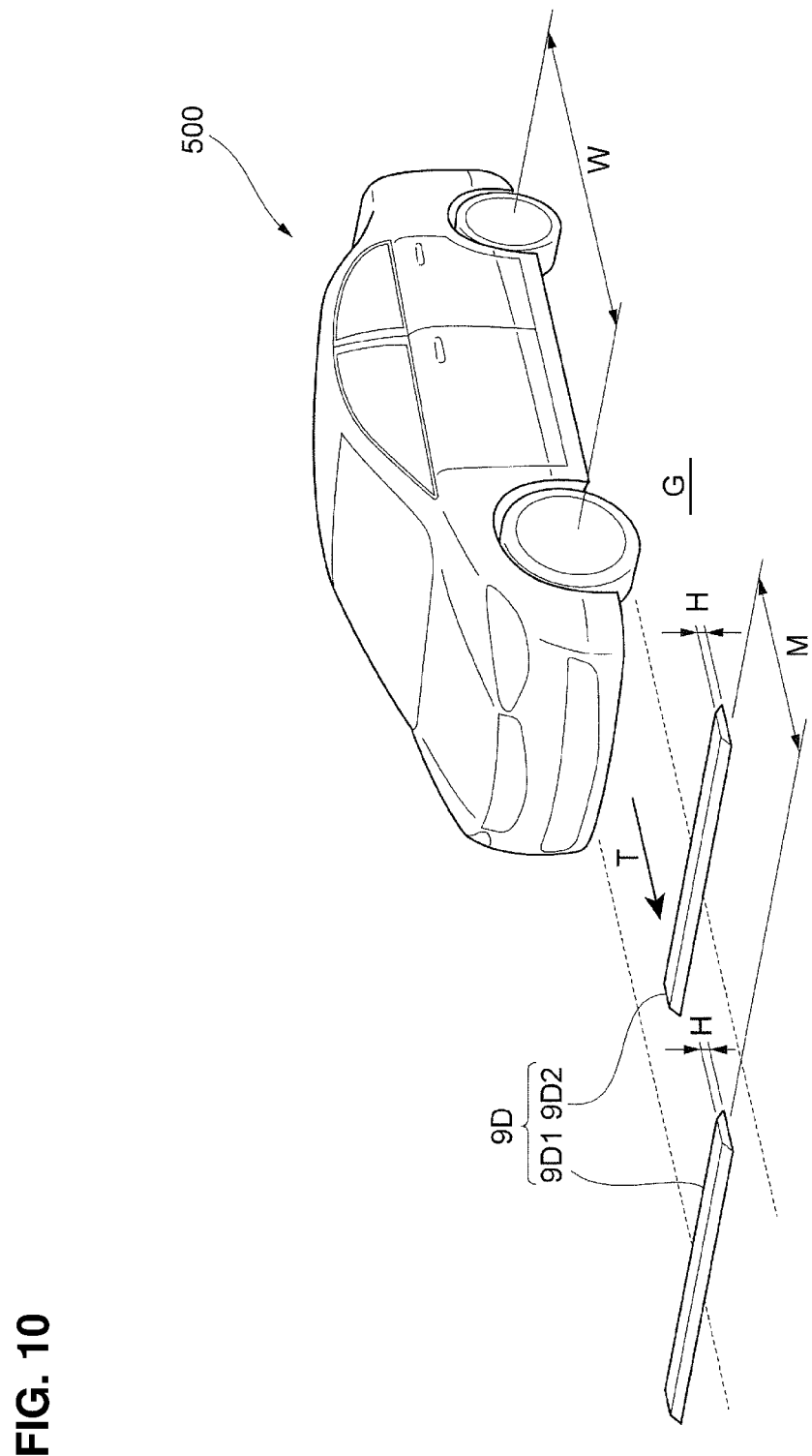
FIG. 10 is a view showing a vehicle load input mechanism serving as a step by which up-and-down movements are given to the vehicle running on a substantially horizontal ground surface.

In FIG. 10, a step 9D having a height H by which up-and-down movements are given to the vehicle 500 running on the substantially horizontal ground surface G is arranged on the ground surface G. The step 9D is an example of the vehicle load input mechanism.

As a method for causing the vehicle 500 to run and get over a step, a shape shown in FIG. 10 may be, for example, applied.

When the wheels of the vehicle 500 running on the ground surface G get over the step 9D, the wheels of the vehicle 500 are moved so as to be thrust upward from below. Therefore, the dampers 100, 200, 300, and 400 (see FIG. 6) are caused by the step 9D to perform the operation of the compression stroke.

Note that when the vehicle 500 gets down the step 9D, the wheels of the vehicle 500 are moved so as to fall from top to bottom. Therefore, the dampers 100, 200, 300, and 400 are caused by the step 9D to perform the operation of extension stroke.

The step 9D having the shape shown in FIG. 10 is provided with a right step 9D1 having a height H at which the right wheels of the vehicle 500 get over and a left step 9D2 having a height H at which the left wheels of the vehicle 500 get over. Further, the right step 9D1 and the left step 9D2 are arranged at positions deviated from each other in a traveling direction T of the vehicle.

Since the right step 9D1 and the left step 9D2 are arranged at the positions deviated from each other as described above, it is possible to delay a timing at which the right front wheel gets over the right step 9D1 from a timing at which the left front wheel gets over the left step 9D2. Similarly, with the configuration in which the right step 9D1 and the left step 9D2 are arranged at the positions deviated from each other, it is possible to delay a timing at which the right rear wheel gets over the right step 9D1 from a timing at which the left rear wheel gets over the left step 9D2.

A deviation amount M between the right step 9D1 and the left step 9D2 is not preferably equal to a wheel base W of the vehicle 500. With the shape shown in FIG. 10, the deviation amount M between the right step 9D1 and the left step 9D2 is set to be shorter than the wheel base W of the vehicle 500. Thus, it is possible to delay the timing at which the right front wheel of the vehicle 500 gets over the right step 9D1 from the timing at which the left rear wheel of the vehicle 500 gets over the left step 9D2. Note that the deviation amount M between the right step 9D1 and the left step 9D2 may be set to be longer than the wheel base W of the vehicle 500.

In the present invention, the timings at which the respective wheels of the vehicle 500 get over any of the steps 9D1 and 9D2 are not necessarily delayed from each other unlike the above embodiment. Accordingly, the right step 9D1 and the left step 9D2 may be linearly arranged at the same position in the traveling direction T. In this case, the right step 9D1 and the left step 9D2 in this embodiment may be formed into one step integrated so as to linearly extend.

Note that a step shape is not particularly limited. That is, a step having a trapezoidal cross section when seen from a direction perpendicular to the traveling direction T as shown in FIG. 10, or a step having other shapes, for example, a step having a triangular cross section or the like may be employed. In addition, heights (from the ground) of steps may be different between the right and left steps. Moreover, a surface on which the wheels of the vehicle 500 pass through may be further provided with irregularities. Note that right and left steps may be provided at the same position with respect to the traveling direction T. In short, any step that allows the vertical load F1 to be input to the vehicle 500 (see FIG. 6 or the like) due to its vertical interval may be employed.

A method for imposing the vertical load F1 on the vehicle 500 is not limited to the above methods. That is, any method may be employed so long as it allows the vertical load F1 to be imposed on the vehicle 500 so as to operate the dampers 100, 200, 300, and 400 (see FIG. 6).

(Variation 2: Input Load by Wheel Stop Operation)

Figure 11:
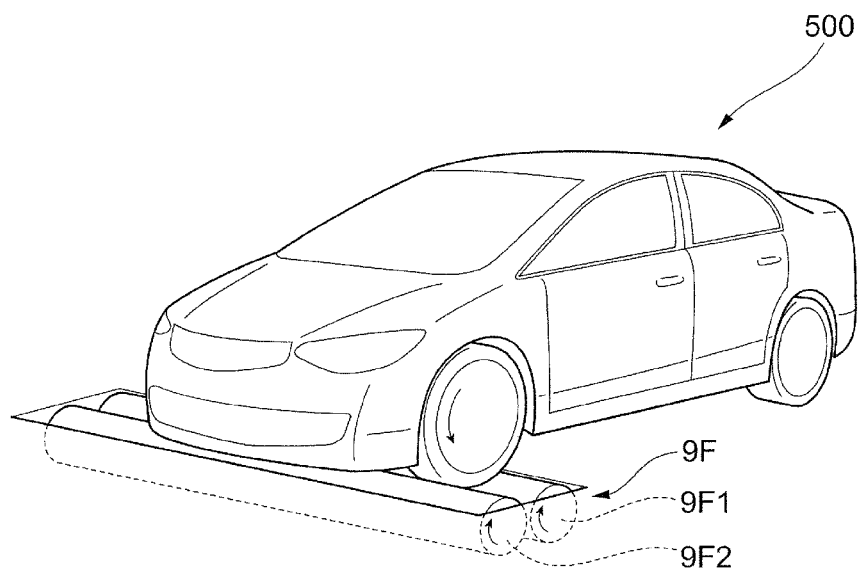
FIG. 11 is a view showing an example of a method for inputting a load to the vehicle with a so-called brake tester.

FIG. 11 is a view showing an example of a method for inputting a load to the vehicle 500 to operate the dampers 100, 200, 300, and 400 with a so-called brake tester 9F (see FIG. 6).

As a method for inputting a load to the vehicle 500 by a stop operation in a state in which the vehicle 500 is caused to run to operate the dampers 100, 200, 300, and 400, the wheels of the vehicle 500 are arranged between a pair of rollers 9F1 and 9F2 of the brake tester 9F, and the wheels are rotated with the rotation of the rollers 9F1 and 9F2 as shown in FIG. 11. When the rotation of the wheels is stopped by the braking operation of a brake in a state in which the wheels are rotated, the wheels of the vehicle 500 are moved so as to be thrust upward from below, and the brake tester 9F causes the dampers 100, 200, 300, and 400 (see FIG. 6) to perform the operation of the compression stroke.

On the other hand, when the braking operation is cancelled in the state in which the rotation of the wheels is stopped, the stopped state of the wheels is cancelled to move the wheels of the vehicle 500 so as to fall from top to below, and the brake tester 9F causes the dampers 100, 200, 300, and 400 to perform the operation of the extension stroke.

Note that in FIG. 11, stroke sensors 6a, 6b, 6c, and 6d (see FIG. 14 that will be described later) that detect extension/compression amounts of the dampers 100, 200, 300, and 400 corresponding to the respective wheels of the vehicle 500 that will be described later are exemplified as expansion/contraction detectors. However, other detection devices may be provided.

(Variation in Detection Device)

(Variation 1: Determination Based on the Number of Inflection Points) As a method for determining the wheel load meter 4 (see FIG. 6) by the output device 3 in the second embodiment, it is possible to employ a determination based on the number of inflection points occurring in a curve showing a change in a wheel load obtained by the wheel load detection units 4a, 4b, 4c, and 4d.

Figure 12:
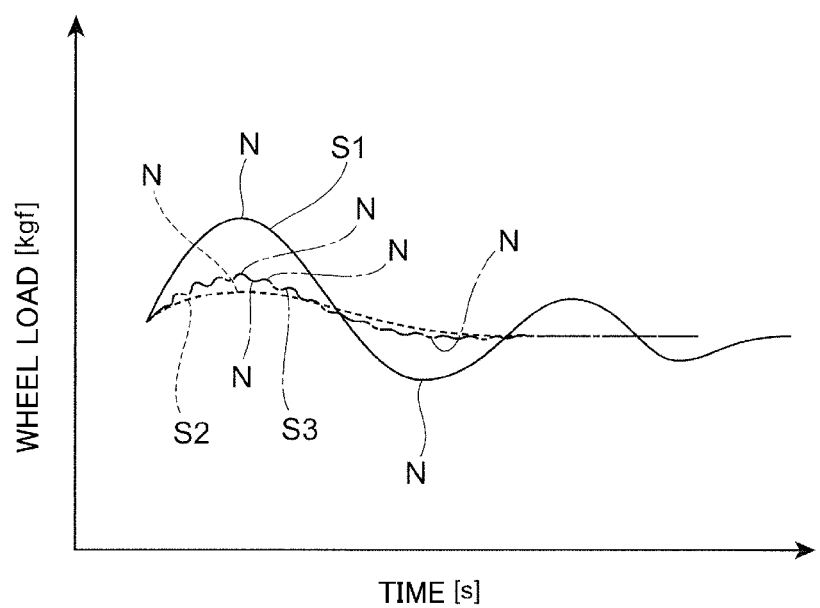
FIG. 12 is a diagram showing a change in a wheel load relative to elapsed time when an input for operating the dampers is given.

That is, FIG. 12 is a diagram showing a change in a wheel load ((kgf): vertical axis) detected by the wheel load detection units 4a, 4b, 4c, and 4d relative to elapsed time ((second): horizontal axis) when an input for operating the dampers 100, 200, 300, and 400 (see FIG. 6) is given. A curve S1 in FIG. 12 shows a temporal change in a wheel load when the dampers 100, 200, 300, and 400 generate a high damping force, a curve S2 shows a temporal change in a wheel load when the dampers 100, 200, 300, and 400 generate a low damping force, and a curve S3 shows a temporal change in a wheel load when each of the damping force variable mechanisms 50 normally operates.

A wheel load corresponding to each of the dampers 100, 200, 300, and 400 detected by each of the wheel load detection units 4a, 4b, 4c, and 4d is stored in the storage unit 3f (see FIG. 5).

When the damping force variable mechanisms 50 normally operate, the curve S3 showing the temporal change in the wheel load detected by the wheel load detection units 4a, 4b, 4c, and 4d has many inflection points N caused when a high damping force and a low damping force are switched to each other. When the frequency of a change in the level of a current is 10 (Hz), the number n of the inflection points N is, for example, 10 or more (points per second).

On the other hand, when the damping force variable mechanisms 50 do not normally operate, the temporal change in the wheel load detected by the wheel load detection units 4a, 4b, 4c, and 4d is the same as that of the curve S1 or the curve S2. Accordingly, the number n of the inflection points N in the temporal-change curve is smaller than that of the inflection points N when the damping force variable mechanisms 50 normally operate (=10 or more (points per second) (for example, when the frequency of the change in the level of the current is 10 (Hz))).

The determination unit 3g (see FIG. 5) of the output device 3 counts the number n of the inflection points N per elapsed time based on a wheel load input from each of the wheel load detection units 4a, 4b, 4c, and 4d and stored in the storage unit 3f, and determines whether the number n of the counted inflection points N exceeds a threshold n0 set and stored in advance in the storage unit 3f.

For example, the threshold n0 is a value about half the cycle, i.e., 10 (Hz) of the change in the level of the current input from the signal input device 1A to the damping force variable mechanisms 50 (=5 (points per second)). The threshold n0 is only required to be a value or a range by which it is possible to discriminate whether the damping force variable mechanisms 50 normally operate, and is not limited to the above illustrated value.

When it is determined that the number n of the counted inflection points N exceeds the threshold n0 (n0≤n), the determination unit 3g determines that the damping force variable mechanisms 50 normally operate and causes the lamps 2a, 2b, 2c, and 2d to emit green light. When it is determined that the number n of the counted inflection points N is below the threshold n0 (n<n0), the determination unit 3g determines that the damping force variable mechanisms 50 do not normally operate. Therefore, the determination unit 3g does not cause the lamps 2a, 2b, 2c, and 2d to emit light.

Thus, the examination system 700 (see FIG. 6) is allowed to examine the damping force variable mechanisms 50 in a state in which the dampers 100, 200, 300, and 400 are installed in the vehicle 500.

Note that the operation of the variation in the embodiment also includes: the operation step of operating the dampers 100, 200, 300, and 400 in a state in which the dampers 100, 200, 300, and 400, each of which is provided with the damping force variable mechanism 50 that changes a damping force according to an input signal, are installed in the vehicle 500; and the detection step of detecting a wheel load as a change occurring in the vehicle 500 due to the operation step. Further, in the operation step, the dampers 100, 200, 300, and 400 are operated in a state in which a variable signal is input to the damping force variable mechanisms 50 by the signal input device 1A. Accordingly, each of the operations of the variation corresponds to the embodiment of the examination method for the damping force variable mechanism of the present invention.

Further, according to the examination method corresponding to each of the operations of the variation, an examination as to whether the damping force variable mechanisms 50 are normal is allowed in a state in which the dampers 100, 200, 300, and 400 are installed in the vehicle 500.

(Variation 2: Determination Based on Comparison Between Right Wheel and Left Wheel)

As a method for determining the wheel load meter 4 (see FIG. 6) by the output device 3 in the second embodiment, it may be possible to compare a signal output from the wheel load detection unit 4a corresponding to the damper 100 of the right front wheel with a signal output from the wheel load detection unit 4b corresponding to the damper 200 of the left front wheel to determine whether the damping force variable mechanisms 50 of the dampers 100 and 200 are normal based on the difference between the signals.

When the damping force variable mechanisms 50 are normal, the profiles of the signal output from the wheel load detection unit 4a corresponding to the damper 100 of the right front wheel and the signal output from the wheel load detection unit 4b corresponding to the damper 200 of the left front wheel agree with each other even if there is a phase deviation between the signals. On the other hand, when one of the damping force variable mechanisms 50 is abnormal, the profiles of the signals output from both the wheel load detection units 4a and 4b do not agree with each other.

In view of this, the determination unit 3g (see FIG. 5) is configured to determine that both the damping force variable mechanisms 50 normally operate when the profiles of the signal output from the wheel load detection unit 4a corresponding to the damper 100 of the right front wheel and the signal output from the wheel load detection unit 4b corresponding to the damper 200 of the left front wheel agree with each other and configured to determine that at least one of the damping force variable mechanisms 50 does not normally operate when the profiles do not agree with each other. Thus, the examination system 700 is allowed to examine the damping force variable mechanisms 50 in a state in which the dampers 100 and 200 are installed in the vehicle 500.

When the determination unit 3g compares a signal output from the damping force variable mechanism 50 of the damper 300 of the right rear wheel with a signal output from the damping force variable mechanism 50 of the damper 400 of the left rear wheel in the same way, the examination system 700 is also allowed to examine the damping force variable mechanisms 50 in a state in which the dampers 300 and 400 are installed in the vehicle 500.

(Variation 3: Determination Based on Comparison with Reference Value)

As a method for determining the wheel load meter 4 (see FIG. 6) by the output device 3 in the second embodiment, it may be possible to employ a method for making a determination based on the comparison between a reference value output when the damping force variable mechanisms 50 normally operate and an actually output value.

For example, the storage unit 3f (see FIG. 5) of the output device 3 of the wheel load meter 4 stores the reference profile (hereinafter called a model curve) of a signal to be output from the wheel load detection units 4a, 4b, 4c, and 4d when the damping force variable mechanisms 50 are normal. The model curve may be obtained experimentally or statistically.

The determination unit 3g compares the profile of a signal actually detected from each of the damping force variable mechanisms 50 with the model curve.

Then, when the profile of the actually detected signal falls within ±x % of the model curve (where x is a value set in advance as a normal range) as a result of the comparison, the determination unit 3g determines that the damping force variable mechanisms 50 normally operate.

On the other hand, when the profile of the actually detected signal does not fall within ±x % of the model curve, the determination unit 3g determines that the damping force variable mechanisms 50 do not normally operate.

Thus, the examination system 700 is allowed to examine the damping force variable mechanisms 50 in a state in which the dampers 100, 200, 300, and 400 are installed in the vehicle 500.

(Variation 4: Detection Device (Determination Based on Comparison with Reference Value of Change Amount))

As a method for determining the wheel load meter 4 (see FIG. 6) by the output device 3 in the second embodiment, it may be possible to employ a method based on the comparison between a reference value of a change amount (reference change amount) of an output in a certain time and a change amount of an actual output when the damping force variable mechanisms 50 normally operate.

For example, the storage unit 3f (see FIG. 5) of the output device 3 of the wheel load meter 4 stores a reference change amount in a certain time of a signal to be output from the wheel load detection units 4a, 4b, 4c, and 4d when the damping force variable mechanisms 50 are normal.

The determination unit 3g compares a change amount in a certain time of a signal actually detected from each of the damping force variable mechanisms 50 with the reference change amount stored in the storage unit 3f.

Then, when the change amount in the certain time of the actually detected signal is greater or smaller than the reference change amount as a result of the comparison, the determination unit 3g determines that the damping force variable mechanisms 50 do not normally operate. On the other hand, when the change amount in the certain time of the actually detected signal agrees with the reference change amount, the determination unit 3g determines that the damping force variable mechanisms 50 normally operate.

Thus, the examination system 700 (see FIG. 6) is allowed to examine the damping force variable mechanisms 50 in a state in which the dampers 100, 200, 300, and 400 are installed in the vehicle 500.

Note that a size of a folding point in the profile of a detected signal may be used as a comparison target instead of a change amount in a certain time of a signal.

Note that the operation of the variation in the embodiment also includes: the operation step of operating the dampers 100, 200, 300, and 400 in a state in which the dampers 100, 200, 300, and 400, each of which is provided with the damping force variable mechanism 50 that changes a damping force according to an input signal, are installed in the vehicle 500; and the detection step of detecting a wheel load as a change occurring in the vehicle 500 due to the operation step. Accordingly, each of the operations of the variation corresponds to the embodiment of the examination method for the damping force variable mechanism of the present invention.

Further, according to the examination method corresponding to each of the operations of the variation, an examination as to whether the damping force variable mechanisms 50 are normal is allowed in a state in which the dampers 100, 200, 300, and 400 are installed in the vehicle 500.

(Variation 5: Determination Based on Difference Between Load Detected by High Damping Force and Load Detected by Low Damping Force)

As a method for determining the wheel load meter 4 (see FIG. 6) by the output device 3 in the second embodiment, it may be possible to determine whether each of the damping force variable mechanisms 50 of the dampers 100, 200, 300, and 400 is normal based on the difference between a load detected corresponding to a high damping force and a load detected corresponding to a low damping force.

In this case, as signals to be input to each of the damping force variable mechanisms 50 of the dampers 100, 200, 300, and 400, a signal corresponding to the high damping force and a signal corresponding to the low damping force may be separately input.

Specifically, the signal input device 1A shown in FIG. 6 may be replaced by a signal input device 1B indicated by parentheses.

An example of the signal input device 1B switches between a plurality of mutually different currents (an example of a current) and inputs the selected one of the currents to the damping force variable mechanisms 50. Examples of the plurality of currents include a high current by which the dampers 100, 200, 300, and 400 are caused to produce the high damping forces of the characteristic curves f1 and f3 (see FIG. 3) and a low current by which the dampers 100, 200, 300, and 400 are caused to produce the low damping forces of the characteristic curves f2 and f4.

Note that the controller 510 may be used instead of the signal input device 1B so long as the controller 510 is allowed to switch between the high current and the low current to be output from the signal input device 1B and output the selected one of the currents.

In this case, first, the vertical load F1 is imposed in a state in which a high current is input to the damping force variable mechanisms 50 by the signal input device 1B, and a wheel load of each of the wheels is detected by each of the wheel load detection units 4a, 4b, 4c, and 4d until a certain time elapses. Each of the detected wheel loads is input to the output device 3 and stored in the storage unit 3f (see FIG. 5). Next, the vertical load F1 is imposed in a state in which a low current is input to the damping force variable mechanisms 50 by the signal input device 1B, and a wheel load of each of the wheels is detected by each of the wheel load detection units 4a, 4b, 4c, and 4d until a certain time elapses. Each of the detected wheel loads is input to the output device 3 and stored in the storage unit 3f.

Note that the high current and the low current may be input in an order opposite to the above order.

Figure 13:
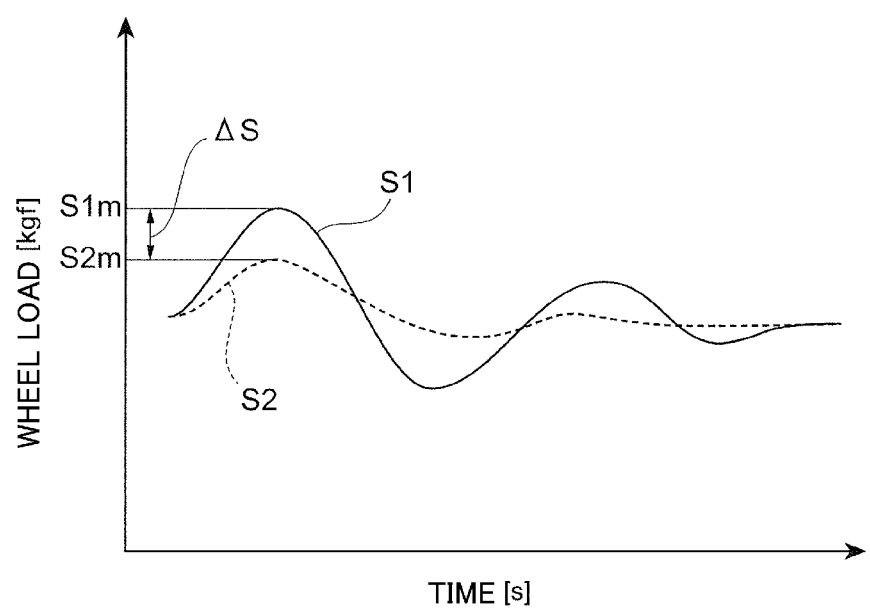
FIG. 13 is a diagram showing a change in a wheel load relative to elapsed time when the same input for operating the dampers is given in a state in which the dampers are allowed to produce a high damping force and a low damping force.

FIG. 13 is a diagram showing a change in a wheel load ((kgf): vertical axis) corresponding to the dampers 100, 200, 300, and 400 relative to elapsed time ((second): horizontal axis) when the same input for operating the dampers 100, 200, 300, and 400 (see FIG. 6) is given in a state in which the dampers 100, 200, 300, and 400 are allowed to produce a high damping force and a low damping force. A curve S1 indicated by a solid line and a curve S2 indicated by dashed lines in FIG. 13 show a temporal change in a wheel load when the dampers 100, 200, 300, and 400 produce a high damping force and a temporal change in a wheel load when the dampers 100, 200, 300, and 400 produce a low damping force, respectively. When the damping force variable mechanisms 50 normally operate, the curve S1 and the curve S2 are different from each other. Particularly, a large difference $\Delta S$ occurs between a maximum value $S1m$ of the wheel load in the curve S1 and a maximum value $S2m$ of the wheel load in the curve S2.

The determination unit 3g (see FIG. 5) of the output device 3 selects the maximum value $S1m$ of the wheel load corresponding to a high current and the maximum value $S2m$ of the wheel load corresponding to a low current, the wheel loads being stored in the storage unit 3f. Then, the determination unit 3g calculates the difference $\Delta S$ between the two selected maximum values $S1m$ and $S2m$ ($=|S2m-S1m|$) and compares the difference $\Delta S$ with a threshold Sk stored in the storage unit 3f.

The threshold Sk is set as a value making it possible to determine whether a substantial difference exists between the maximum value $S1m$ and the maximum value $S2m$. When it is determined that the substantial difference exists, a damping force generated by the dampers 100, 200, 300, and 400 may be determined to be normally switched between a high damping force and a low damping force. On the other hand, when it is determined that the substantial difference does not exist, a damping force generated by the dampers 100, 200, 300, and 400 is not normally switched between a high damping force and a low damping force.

The determination unit 3g determines that the substantial difference exists between the maximum value S1$m$ and the maximum value S2$m$ when a result of the comparison between the difference ΔS and the threshold Sk shows that the difference ΔS is greater than or equal to the threshold Sk (Sk≤ΔS), and determines that the damping force variable mechanisms 50 normally operate since the damping force generated by the dampers 100, 200, 300, and 400 is switched between the high damping force and the low damping force. Thus, the determination unit 3g causes the lamps 2a, 2b, 2c, and 2d to limit green light.

The determination unit 3g determines that the substantial difference does not exist between the maximum value S1$m$ and the maximum value S2$m$ when the result of the comparison shows that the difference ΔS is less than the threshold Sk (ΔS<Sk), and determines that the damping force variable mechanisms 50 do not normally operate since the damping force generated by the dampers 100, 200, 300, and 400 is not normally switched between the high damping force and the low damping force. Thus, the determination unit 3g does not cause the lamps 2a, 2b, 2c, and 2d to emit light.

According to the examination system 700 as described above, the damping force variable mechanisms 50 can be examined in a state in which the dampers 100, 200, 300, and 400 are installed in the vehicle 500.

(Variation Corresponding to Type of Output)

In the second embodiment and the modified examples (the variations 1 to 5) described above, a change in the vehicle 500 in the detection step is detected using the wheel load meter 4 as a detection device. However, the present invention is not limited to such embodiments. That is, in the second embodiment and the modified examples described above, a change in the vehicle 500 in the detection step may be detected using a damper stroke detection device 6 shown in FIG. 14 instead of the wheel load meter 4.

Here, as shown in FIG. 14, the damper stroke detection device 6 (an example of an extension/compression amount detection device) is provided with the stroke sensors 6a, 6b, 6c, and 6d that detect extension/compression amounts of the dampers 100, 200, 300, and 400, respectively, corresponding to the wheels of the vehicle 500, the output device 3, and the harness 523. In this case, each of the strokes of the dampers 100, 200, 300, and 400 is an example of an output from a vehicle in the present invention.

Note that it may also be possible to perform a detection step using other detection devices allowed to detect a change in an output from the vehicle 500. The detection devices are allowed to detect a change in the vehicle 500 based on a detection value corresponding to a change amount of an output accompanied by the change in the vehicle 500.

The operation of the variation in the embodiment also includes: the operation step of operating the dampers 100, 200, 300, and 400 in a state in which the dampers 100, 200, 300, and 400, each of which is provided with the damping force variable mechanism 50 that changes a damping force according to an input signal, are installed in the vehicle 500; and the detection step of detecting a wheel load or extension/compression amounts of the dampers 100, 200, 300, and 400 as a change occurring in the vehicle 500 due to the operation step. Further, in the operation step, the dampers 100, 200, 300, and 400 are operated in a state in which a plurality of mutually different signals is switched and input to the damping force variable mechanisms 50 by the signal input device 1B. Accordingly, each of the operations of the variation corresponds to the embodiment of the examination method for the damping force variable mechanism of the present invention.

Further, according to the examination method corresponding to each of the operations of the variation, an examination as to whether the damping force variable mechanisms 50 are normal is allowed in a state in which the dampers 100, 200, 300, and 400 are installed in the vehicle 500.

In addition, a detection device that mechanically detects pressure or a sound may be employed. Moreover, in the detection step of the present invention, a person may detect a change in pressure or a sound using the five senses instead of using a detection device.

Hereinafter, an examination method and an examination system for the damping force variable mechanisms 50 that include the detection step of performing detection using pressure or a sound will be described in detail.

In the operation step of changing an input current in a state in which the vertical load F1 is caused to act on the vehicle 500, an output from the vehicle 500 changes according to the change in the input current. The change in the output from the vehicle 500 emerges as vibrations indicating a change in a reaction force from the dampers 100, 200, 300, and 400 of the vehicle 500. In the examination system and the examination method of the embodiment, the vibrations of the dampers 100, 200, 300, and 400 are detected in the detection step.

That is, in the examination method and the examination system of the embodiment, a detection device such as an oscillator or an examiner vertically downwardly imposes the vertical load F1 on parts near the dampers 100, 200, 300, and 400 as examination targets of the vehicle 500 to operate the dampers 100, 200, 300, and 400 at a speed of Va (m/s) (operation step). At this time, a current that changes between high and low levels (see, for example, FIG. 7A) is input to the damping force variable mechanisms 50 of the dampers 100, 200, 300, and 400. The current that changes between high and low levels is input by, for example, the signal input device 1A shown in FIG. 6.

Accordingly, when the damping force variable mechanisms 50 normally operate, a damping force f(N) at a speed of Va (m/s) of the dampers 100, 200, 300, and 400 changes between the high damping force f3$a$ (N) and the low damping force f4$a$ (N) in the compression stroke as shown in FIG. 3 according to a change in the input current. The change in the damping force f(N) in the compression stroke corresponds to a change in an "output from a vehicle" in the present invention.

In addition, the cycle of the change in the damping force f corresponds to the cycle of the change in the current input to the damping force variable mechanisms 50. Therefore, the cycle of the change in the damping force f in the embodiment is 10 (Hz).

As described above, according to the examination method and the examination system of the embodiment, during a period in which a detection device such as an oscillator or an examiner vertically downwardly imposes the vertical load F1 on the vehicle 500 to operate the dampers 100, 200, 300, and 400 at a speed of Va (m/s), the damping force f of the dampers 100, 200, 300, and 400 changes between the high damping force f3$a$ (N) and the low damping force f4$a$ (N) at a certain cycle. Accordingly, a reaction force against the vertical load F1 that the detection device or the examiner receives from the vehicle 500 in the detection step changes.

As a result, the detection device is allowed to detect the change in the reaction force, or the examiner pushing the vehicle 500 by hand is allowed to feel the change in the reaction force by hand as pressure sense (tactile sense).

On the other hand, there is a likelihood that the movement of the valve body of the solenoid valve 51 is not allowed when the solenoid valve 51 (see FIG. 2) is clogged with dust or the like generated in oil. In this case, the damping force variable mechanism 50 is not allowed to change a damping force.

When the dampers 100, 200, 300, and 400, the damping force of which does not change as described above, are examined by the examination system and the examination method of the embodiment, a reaction force against the vertical load F1 that the detection device or the examiner receives from the vehicle 500 in the detection step does not change. As a result, the detection device is not allowed to detect a change in the reaction force, or the examiner pushing the vehicle 500 by hand is not allowed to feel the change in the reaction force by hand as pressure sense (tactile sense).

As described above, according to the examination system and the examination method for the damping force variable mechanisms 50 of the dampers 100, 200, 300, and 400 of the embodiment, the damping force variable mechanisms 50 of the dampers 100, 200, 300, and 400 can be examined in a state in which the damping force variable mechanisms 50 of the dampers 100, 200, 300, and 400 are installed in the vehicle 500.

In addition, according to the examination system and the examination method for the damping force variable mechanisms 50 of the dampers 100, 200, 300, and 400 of the embodiment, a determination as to whether a change occurs in a damping force of the dampers 100, 200, 300, and 400 is allowed based on a value detected by the detection device or an examiner's feeling (pressure sense) about a reaction force received by the examiner. Then, when the detection device detects the change or when the examiner feels the change in the reaction force, the examiner is allowed to determine that the damping force variable mechanisms 50 normally operate. On the other hand, when the detection device does not detect the change or when the examiner does not feel the change in the reaction force, the examiner is allowed to determine that the damping force variable mechanisms 50 do not normally operate.

Moreover, according to the examination system and the examination method for the damping force variable mechanisms 50 of the dampers 100, 200, 300, and 400 of the embodiment, a change in a reaction force received by the examiner has a constant cycle corresponding to a change in an input current. Therefore, the change in the reaction force is easily detected.

The examination system and the examination method for the damping force variable mechanisms 50 of the dampers 100, 200, 300, and 400 of the embodiment output a change in a reaction force from the vehicle 500, i.e., vibrations of the dampers 100, 200, 300, and 400 that may be determined based on a value detected by the detection device or examiner's pressure sense in the detection step. However, the examination system and the examination method for the damping force variable mechanism according to the present invention are not limited to the embodiment.

That is, as another embodiment, the examination system and the examination method of the present invention may be such that a change occurring in the output of the vehicle 500 according to a change in an input current is expressed by, for example, the presence or absence of a sound emitted from the damping force variable mechanisms 50 of the dampers 100, 200, 300, and 400 of the vehicle 500 and the presence or absence of the sound is output to an examiner as a detection value of the detection device or auditory sense in the detection step.

In the solenoid valve 51 of the damping force variable mechanism 50 in each of the dampers 100, 200, 300, and 400 as examination targets of the embodiment, the excitation force of the fixed core by the coil (not shown) of the solenoid valve 51 changes with the input of the variable current shown in FIGS. 7A to 7D. That is, when a high current (for example, a current of 0.8 (A) at which a high damping force is generated) is fed to the coil, a relatively high excitation force is generated in the fixed core, whereby the magnetic body (not shown) of the solenoid valve 51 is strongly attracted to the fixed core.

Further, an attraction force by the fixed core to the magnetic body is set to be greater than the total sum of pressure generated in the flow path of oil and an initial pressing force acting on the magnetic body (for example, an elastic force by an elastic body such as a spring) in the compression stroke of the dampers 100, 200, 300, and 400. Accordingly, when the high current is fed to the damping force variable mechanism 50, the magnetic body collides with the fixed core in the compression stroke of the dampers 100, 200, 300, and 400 in which pressure acts on the flow path. A hammering sound is generated when the magnetic body collides with the fixed core.

On the other hand, when a low current (for example, a current of 0.3 (A) at which a low damping force is generated) is fed, a relatively low excitation force is generated in the fixed core, whereby the magnetic body is weakly attracted to the fixed core.

Further, an attraction force by the fixed core to the magnetic body is set to be smaller than the total sum of the pressure generated in the flow path and an initial pressing force acting on the magnetic body in the compression stroke of the dampers 100, 200, 300, and 400. Accordingly, when the low current is fed to the damping force variable mechanism 50, the magnetic body does not collide with the fixed core in the compression stroke of the dampers 100, 200, 300, and 400 in which pressure acts on the flow path. Thus, no hammering sound is generated by the collision.

That is, when the vehicle load input mechanism or the examiner vertically downwardly imposes the vertical load F1 (see FIG. 6) on places near portions of the vehicle 500 at which the dampers 100, 200, 300, and 400 as examination targets are installed, the dampers 100, 200, 300, and 400 are put in the compression stroke in which pressure acts on the flow path.

When the damping force variable mechanisms 50 normally operate in this state, the magnetic body repeatedly collides with and separates from the fixed core with a change in the level of a current input to the damping force variable mechanisms 50. Then, a hammering sound is generated when the magnetic body is switched from the state in which the magnetic body separates from the fixed core to the state in which the magnetic body collides with the fixed core.

On the other hand, when the damping force variable mechanisms 50 do not normally operate, no hammering sound is generated even if the current input to the damping force variable mechanisms 50 changes in the compression stroke of the dampers 100, 200, 300, and 400.

Accordingly, the detection device determines the presence or absence of a hammering sound based on a detected value or the examiner determines the same with auditory sense in the detection step. Thus, the examiner is allowed to determine whether the damping force variable mechanisms 50 normally operate.

In addition, when a reaction force from the vehicle 500 is detected by the vehicle body of the vehicle 500, there is a likelihood that not only a change in the damping force of the adjacent damper 100 but changes in the damping forces of the other dampers such as the damper 200 are also transmitted to the vehicle body in an overlapped state. Accordingly, in order to accurately examine each of the dampers 100, 200, 300, and 400, it is preferable to detect a reaction force with wheels and tires as elements under the springs of the vehicle 500, each of which is not directly affected by changes in the damping forces of the other dampers 100, 200, 300, and 400.

EXAMPLES

FIG. 15 is a table showing a list of experimental results in which, compared with a case in which a constant current was input to the damping force variable mechanism 50, a difference in pressure sense and a difference in auditory sense were verified for each of the different combinations of changes in a current input to the damping force variable mechanism 50 and frequencies accompanied by the changes in the above embodiment.

In FIG. 15, in Example 1, a current input to the damping force variable mechanism 50 was changed between 0.3 (A) and 1.6 (A), and the frequency of the change was set at 5 (Hz).

In Example 2, the current input to the damping force variable mechanism 50 was changed between 0.3 (A) and 1.6 (A), and the frequency of the change was set at 10 (Hz).

In Example 3, the current input to the damping force variable mechanism 50 was changed between 0.3 (A) and 0.8 (A), and the frequency of the change was set at 10 (Hz). The Example 3 is the mode illustrated in the description of the above embodiment.

The experimental results show that, in the mode of Example 1, an examiner was allowed to feel a difference in both the pressure sense and the auditory sense in the detection step compared with a case in which a constant current was input to the damping force variable mechanism 50, and allowed to effectively determine whether the damping force variable mechanism 50 was normal through both the pressure sense and the auditory sense.

In addition, in the mode of Example 2, the examiner was allowed to feel a difference in both the pressure sense and the auditory sense in the detection step compared with the case in which the constant current was input to the damping force variable mechanism 50, and allowed to effectively determine whether the damping force variable mechanism 50 was normal through both the pressure sense and the auditory sense.

In the mode of Example 3, the examiner was allowed to feel a difference in both the pressure sense and the auditory sense in the detection step compared with the case in which the constant current was input to the damping force variable mechanism 50, and although the difference was smaller than in Examples 1 and 2, the examiner was allowed to effectively determine whether the damping force variable mechanism 50 was normal through both the pressure sense and the auditory sense.

(Variation in Output Device 3 or the Like)

Each of the detection device 2 (see FIG. 5) and the output device 3 in the detection step causes each of the lamps 2a or the like to emit green light only when it is determined that the damping force variable mechanism 50 is normal. However, the present invention is not limited to this mode. That is, for example, the detection device 2 and the output device 3 may cause each of the lamps 2a or the like to emit red light only when it is determined that the damping force variable mechanism 50 is not normal, or may cause each of the lamps 2a or the like to emit green light when it is determined that the damping force variable mechanism 50 is normal and cause each of the lamps 2a or the like to emit red light when it is determined that the damping force variable mechanism 50 is not normal.

In addition, the detection device 2 and the output device 3 detect a signal in a wired fashion using a harness. However, the present invention is not limited to this mode. That is, the detection device 2 and the output device 3 may detect a signal in a wireless fashion.

The detection device 2 and the output device 3 are provided with the four lamps 2a, 2b, 2c, and 2d each of which corresponds to each of the wheels, but may be provided with only the lamp 2a. In this case, it may be possible that the dampers 100, 200, 300, and 400 (see FIGS. 1 and 6) corresponding to the respective wheels are successively examined by the switching of the rotary switch 2s or the like and the lamp 2a is commonly used to examine all the dampers 100, 200, 300, and 400.

Moreover, the detection device 2 and the output device 3 cause the lamp 2a or the like to emit light as a method for displaying an examination result (as to whether the damping force variable mechanism 50 is normal). However, the present invention is not limited to this mode. That is, for example, the detection device 2 and the output device 3 may display the numbers (numbers, symbols, or the like corresponding to the wheels) of the dampers 100, 200, 300, and 400 determined to be normal or abnormal.

The signal of an examination result as to whether the damping force variable mechanism 50 is normal may be displayed not only on the outside of the vehicle 500 but also on a display unit provided in the vehicle 500 (for example, the display unit of a car navigation system, the monitor of the around monitoring camera of the vehicle, and the displays of other meters).

Further, the signal of the examination result may be presented not only to dedicated equipment but also to general-purpose equipment (for example, a smart phone, a tablet terminal, or the like).

Furthermore, the examination result may be presented not only in a display form based on human's visual stimulation but also in other forms based on auditory stimulation or tactile stimulation.

Note that at least one of the storage unit 2f(3f) and the determination unit 2g(3g) may be provided in the detection device 2 and the output device 3 arranged inside (the vehicle room or the like) of the vehicle 500.

In addition, the detection step in the present invention is the step of detecting an output from a vehicle. However, the output from the vehicle includes various outputs from various devices (the controller 510, the dampers 100, 200, 300, and 400, or the like) and a structure (a vehicle body or the like) constituting the vehicle.

(Variation in Damper)

Both the examination systems 600 and 700 and the examination methods of the above first and second embodiments (including the variations) target at the so-called triple-tube dampers 100, 200, 300, and 400, each of which is provided with the cylinder portion 10 having the cylinder 11 (see FIG. 2) in which oil (an example of hydraulic oil) is included, the outer cylinder 12 provided on the outside of the cylinder 11, and the damper case 13 provided on the outside of the outer cylinder 12, and provided with the damping force variable mechanism 50 that is connected to the cylinder portion 10 and varies a damping force according to an input signal.

However, the examination method and the examination system for the damping force variable mechanism according to the present invention are not limited to those targeting at a triple-tube pressure damping device. That is, the examination method and the examination system for the damping force variable mechanism according to the present invention also cover a pressure damping device having a single cylinder and a pressure damping device having a plurality of cylinders (double tube) so long as they are provided with a damping force variable mechanism.

In addition, the damping force variable mechanism is not limited to one that changes a damping force with the solenoid valve 51, and a damping force variable mechanism that electrically changes a damping force, a damping force variable mechanism that magnetically changes a damping force, and a damping force variable mechanism that mechanically changes a damping force may be used so long as they are allowed to change a damping force using any signal.

Third Embodiment

Next, a third embodiment will be described in detail with appropriate reference to the drawings. Note that in the following description, parts common to the other embodiments will be denoted by the same symbols and their duplicated descriptions will be omitted.

Figure 16:
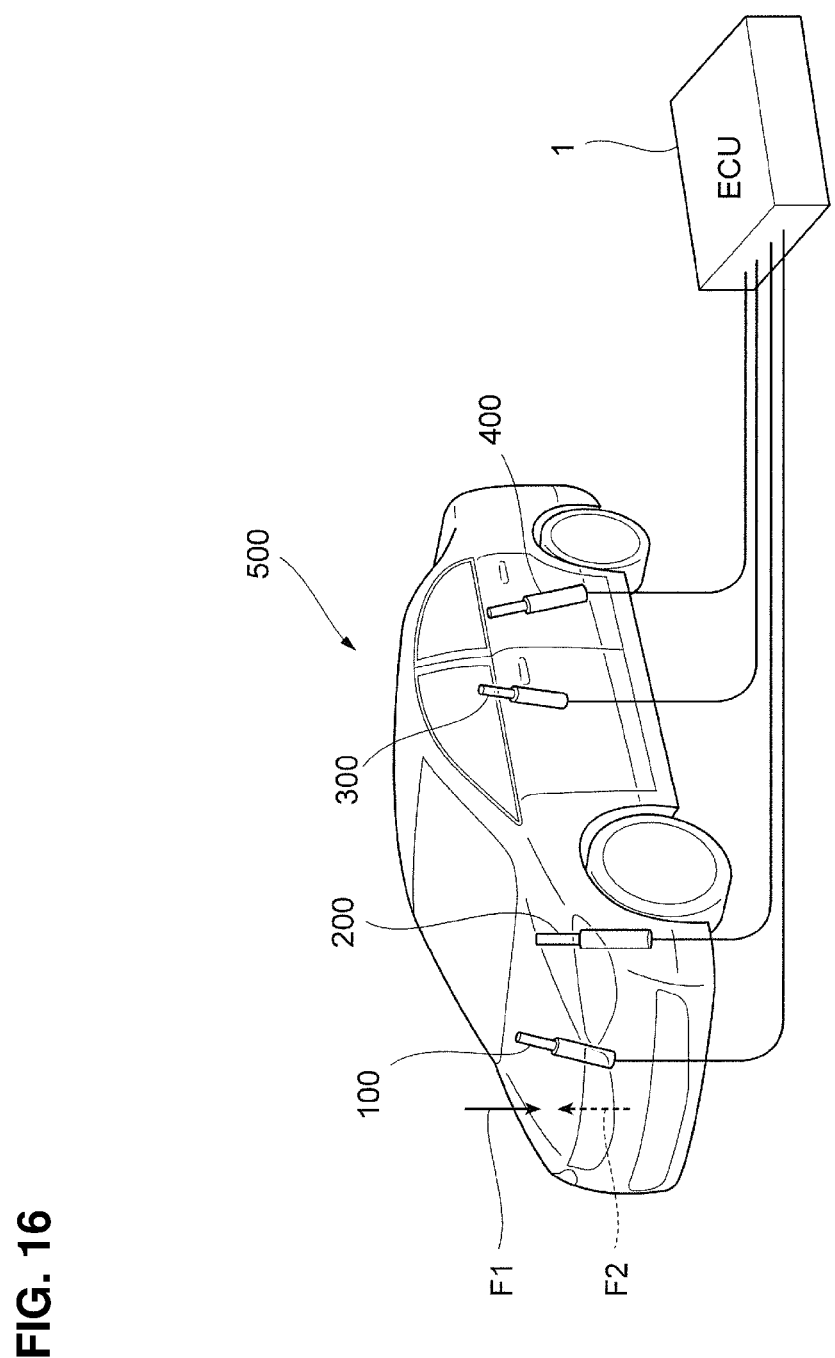
FIG. 16 is a schematic view showing an examination method for the damping force variable mechanisms of pressure damping devices according to a third embodiment.

FIG. 16 is a schematic view showing an examination method for the damping force variable mechanisms 50 of the dampers 100, 200, 300, and 400, each of which is provided with the damping force variable mechanism, according to the third embodiment.

Next, a method for examining a damper (variable damper) according to the third embodiment will be described.

First, the characteristic curve of a damping force f in the extension stroke and the compression stroke of the damper will be described.

Figure 17:
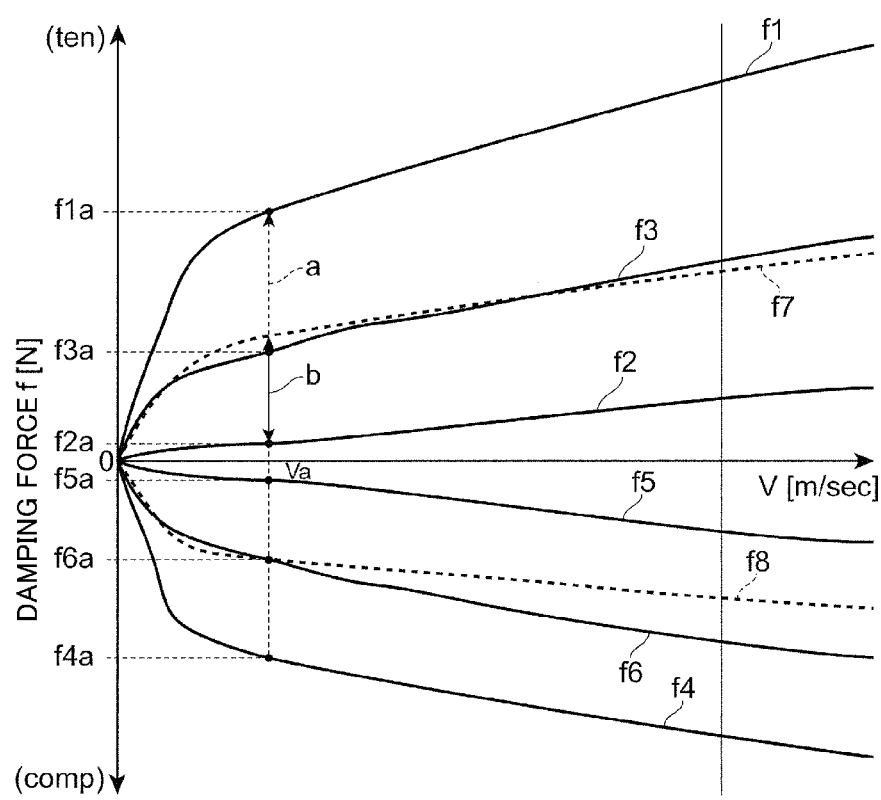
FIG. 17 is a diagram showing an example of the characteristic curves of a damping force in the extension stroke and the compression stroke of the pressure damping device according to the third embodiment.

FIG. 17 is a diagram showing an example of the characteristic curves of the damping force f in the extension stroke and the compression stroke of the damper 100 to which the third embodiment is applied.

(Characteristic Curves at Normal Time)

In FIG. 17, a characteristic curve f1 is a characteristic curve in a case in which a high current (for example, 1.6 (A)) of a maximum damping force normal value is input to the damping force variable mechanism 50 to cause the damper 100 to generate relatively the highest damping force (hereinafter called the maximum damping force) in the extension stroke (ten side).

In FIG. 17, a characteristic curve f2 is a characteristic curve in a case in which a low current (for example, 0.3 (A)) of a minimum damping force normal value is input to the damping force variable mechanism 50 to cause the damper 100 to generate relatively the lowest damping force (hereinafter called the minimum damping force) in the extension stroke.

In FIG. 17, a characteristic curve f3 is a characteristic curve in a case in which a middle current (for example, 0.8 (A)) of a middle damping force normal value is input to the damping force variable mechanism 50 to cause the damper 100 to generate relatively a middle damping force (hereinafter called a middle damping force) in the extension stroke.

On the other hand, in FIG. 17, a characteristic curve f4 is a characteristic curve in a case in which a high current (for example, 1.6 (A)) of a maximum damping force normal value is input to the damping force variable mechanism 50 to cause the damper 100 to generate relatively the highest damping force (hereinafter called the maximum damping force) in the compression stroke (comp side).

In FIG. 17, a characteristic curve f5 is a characteristic curve in a case in which a low current (for example, 0.3 (A)) of a minimum damping force normal value is input to the damping force variable mechanism 50 to cause the damper 100 to generate relatively the lowest damping force (hereinafter called the minimum damping force) of a middle damping force normal value in the compression stroke.

In FIG. 17, a characteristic curve f6 is a characteristic curve in a case in which a middle current (for example, 0.8 (A)) of a middle damping force normal value is input to the damping force variable mechanism 50 to cause the damper 100 to generate relatively a middle damping force (hereinafter called a middle damping force) in the compression stroke.

Here, a high current of a maximum damping force normal value is input from the controller 510 of the vehicle 500 to the damping force variable mechanism 50 to put the damper 100 in a state in which the damper 100 generates the high damping forces of the characteristic curves f1 and f4. When the damper 100 is moved at a speed of, for example, Va (m/s) in this state (the piston rod 20 is moved along the direction of the axis C with respect to the cylinder portion 10), the damper 100 has a damping force of f1$a$ (N) in the extension stroke and a damping force of f4$a$ (N) in the compression stroke.

On the other hand, a low current of a minimum damping force normal value is input from the controller 510 of the vehicle 500 to the damping force variable mechanism 50 to put the damper 100 in a state in which the damper 100 generates the low damping forces of the characteristic curves f2 and f5. When the damper 100 is moved at a speed of, for example, Va (m/s) in this state, the damper 100 has a damping force of f2$a$ (N) in the extension stroke and a damping force of f5$a$ (N) in the compression stroke.

In addition, a middle current of a middle damping force normal value is input from the controller 510 of the vehicle 500 to the damping force variable mechanism 50 to put the damper 100 in a state in which the damper 100 generates the middle damping forces of the characteristic curves f3 and f6. When the damper 100 is moved at a speed of, for example, Va (m/s) in this state, the damper 100 has a damping force of f3$a$ (N) in the extension stroke and a damping force of f6$a$ (N) in the compression stroke.

(At Normal Operation of Damping Force Variable Mechanism 50)

When the damping force variable mechanism 50 normally operates, the damping force f(N) of the damper 100 at a speed of Va (m/s) changes between the high damping force f4$a$ (N) and the low damping force f5$a$ (N) in the compression stroke as shown in FIG. 17 according to a change in an input current. At this time, the damping force f(N) also changes between the middle damping force f6$a$ (N) and the low damping force f5$a$ (N). The change in the damping force f(N) in the compression stroke corresponds to a "change occurring in the vehicle" in the present invention.

In addition, since the cycle of the change in the damping force f(N) corresponds to the cycle of the change in the current input to the damping force variable mechanism 50, the cycle of the change in the damping force f(N) in the third embodiment is 5 (Hz).

In the third embodiment, during a period in which an examiner causes imposes the load F1 to vertically downwardly act on the vehicle 500 twice or so per second to operate the damper 100 at a speed of Va (m/s), the damping force f(N) of the damper 100 changes between the high damping force f4a (N) and the low damping force f5a (N) at a constant cycle. At this time, the damping force f(N) also changes between the middle damping force f6a (N) and the low damping force f5a (N). Accordingly, a reaction force F2 against the load F1 that the examiner receives from the vehicle 500 changes. As a result, the examiner pushing the vehicle 500 by hand is allowed to feel the change in the reaction force F2 by hand as pressure sense (tactile sense). At the normal time, the examiner is allowed to detect the change through pressure sense (tactile sense) and visual sense, for example, when the wheels are jumped up.

For example, there is a likelihood that the movement of the valve body of the solenoid valve 51 is not allowed, for example, when the solenoid valve 51 (see FIG. 2) is clogged with dust or the like generated in oil. In this case, even if the current input to the damping force variable mechanism 50 changes, the damping force of the damper 100 does not change. When the damper 100, the damping force of which does not change, is examined by the examination method of the third embodiment, the examiner does not feel a change in the reaction force F2 against the load F1 that he/she receives from the vehicle 500 by hand as pressure sense (tactile sense).

(Characteristic Curves at Defective Time at which Variable Width Becomes Narrow)

In the examination method for the damper of the third embodiment, a rectangular wave current (or a sine wave current) serving as a MIN-MAX current (first fluctuation current) is basically applied at a frequency of 5 Hz or so as will be described later to oscillate the vehicle 500 (for example, the examiner oscillates the vehicle 500 by hand) to determine whether the damper is put in a defective state.

When the damper 100 put in a normal state is examined by the above examination method, the action or sound of the vehicle 500 changes with a current. On the other hand, for example, when the damping force variable mechanism 50 (a variable valve portion) is clogged, a damping force does not change and the action or sound of the vehicle does not change (for example, the wheels are jumped up as described above when the damper 100 is put in a normal state). By confirming this difference, the examiner is allowed to roughly detect the defective state.

However, there is a likelihood that a defect such as a narrowed variable width of the damper 100 is caused depending on a clogged state or a broken state of the damping force variable mechanism 50 (the variable valve portion). In this case, since a damping force variable function works to a certain extent, the defect may not be detected by the above examination method.

An example in which a defect may not be detected only by the MIN-MAX current will be described.

In FIG. 17, a characteristic curve f7 indicated by dashed lines is a characteristic curve at a defective time at which a variable width of the damper 100 becomes narrow when a high current (for example, 1.6 (A)) of a maximum damping force abnormal value is input to the damping force variable mechanism 50 to cause the damper 100 to have a damping force abnormal value (hereinafter called a maximum damping force abnormal value) in the extension stroke (ten side).

In FIG. 17, a characteristic curve f8 indicated by dashed lines is a characteristic curve at a defective time at which a variable width of the damper 100 becomes narrow when a high current (for example, 1.6 (A)) of a maximum damping force abnormal value is input to the damping force variable mechanism 50 to cause the damper 100 to have a damping force abnormal value (hereinafter called a maximum damping force abnormal value) in the compression stroke (comp side).

As indicated by a dashed arrow a in FIG. 17, when a current alternately switching between a high current (for example, 1.6 (A)) of a maximum damping force normal value showing the characteristic curve of the high damping force f1 and a low current (for example, 0.3 (A)) of a minimum damping force normal value showing the characteristic curve of the low damping force f2 is applied to oscillate the vehicle 500, the damping force variable mechanism 50 of the damper 100 varies unless it is defective.

However, when a defect by which a variable width of the damping force variable mechanism 50 becomes narrow is caused in the damping force variable mechanism 50, the damping force variable mechanism 50 varies only with a damping force indicated by a solid arrow b in FIG. 17 even if a high current (for example, 1.6 (A)) having the same current value as that of a high current (for example, 1.6 (A)) of a maximum damping force normal value is applied. In this case, the detection of such a defect is not allowed only with the applied MIN-MAX current. That is, only with one type of an applied current, it is possible to confirm whether the damping force variable mechanism 50 varies but is not possible to determine whether a variable width of the damping force variable mechanism 50 has become narrow (it is possible to confirm only the presence or absence of the vibrations of the wheels).

In the examination method for the damper of the third embodiment, a plurality of types of currents having different amplitudes is applied to allow the detection of a defect in the damper that varies but is caused to have a narrowed variable width.

Next, the examination method for the damper of the third embodiment will be described in detail.

In the examination method for the damper of the third embodiment, in a state in which the damper 100 provided with the damping force variable mechanism 50 that changes the damping force f(N) according to an input current (an example of a signal) is installed in the vehicle 500 as shown in FIG. 16, the vehicle 500 is oscillated up and down so as to operate the damper 100 with, for example, the input of a signal (current) that changes at high and low amplitudes to cause the examiner to feel a change occurring in the vehicle 500 according to a change in the current input to the damping force variable mechanism 50.

FIGS. 18A to 18E are graphs showing an oscillation amplitude (stroke) (m), a stroke speed (m/s), an applied current (A), a generated damping force (N), and a damping force change rate (N/s) input to the damping force variable mechanism 50, respectively.

(Level of Applied Current)

Figure 18:
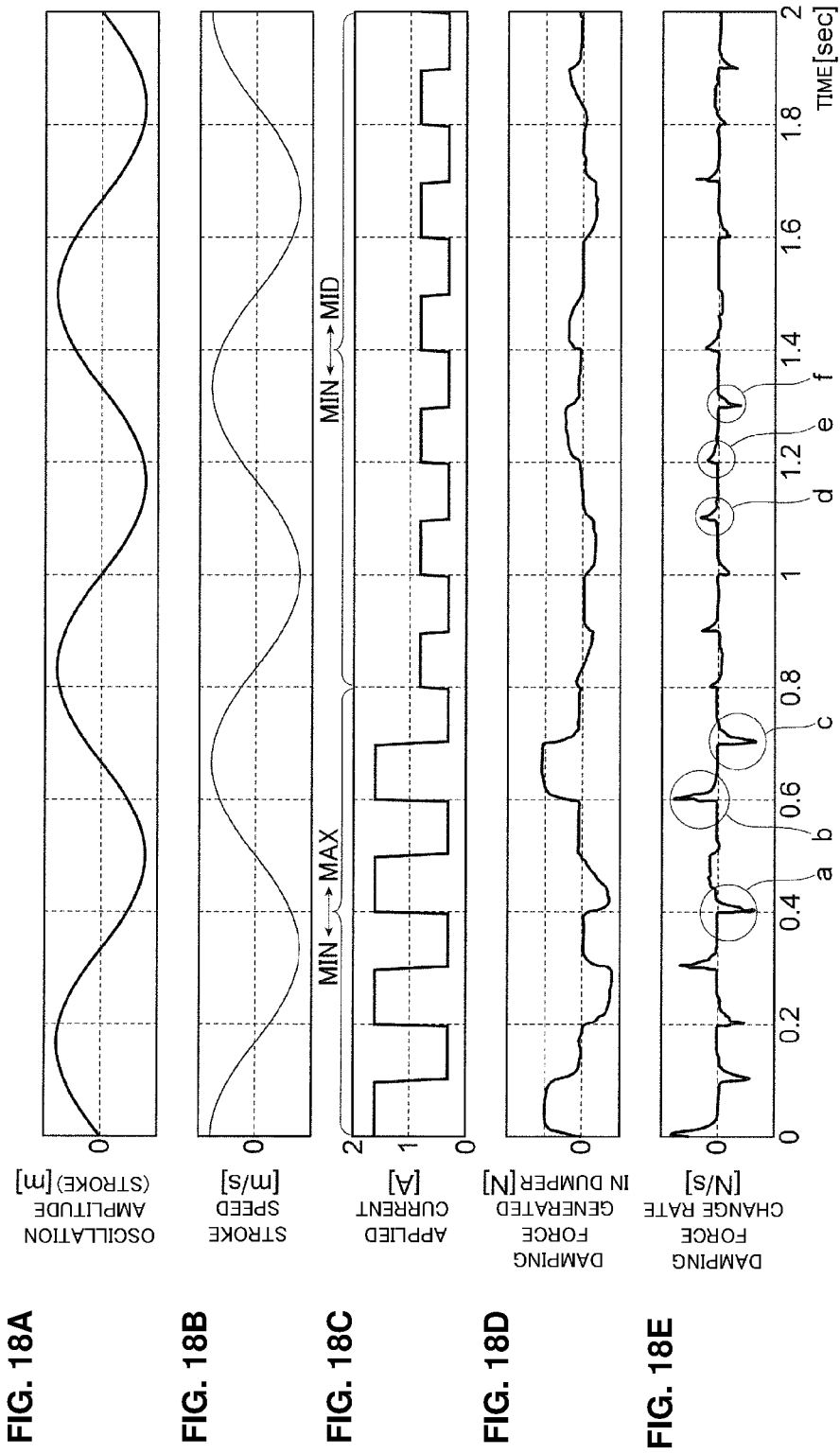
FIGS. 18A to 18E are graphs showing an oscillation amplitude (stroke) (m), a stroke speed (m/s), an applied current (A), a generated damping force (N), and a damping force change rate (N/s) input to the damping force variable mechanism of the pressure damping device according to the third embodiment, respectively.

As shown in the region MIN-MAX of FIG. 18C, the applied current is a current having a large amplitude at which the damper 100 changes such that a high current (for example, 1.6 (A)) showing the characteristic curves (see FIG. 17) of the high damping forces f1 and f4 and a low current (for example, 0.3 (A)) showing the characteristic curves (see FIG. 17) of the low damping forces f2 and f5 are alternately repeated. In addition, as shown in the region MIN-MID of FIG. 18C, the applied current is a current having a middle amplitude at which the damper 100 changes such that a middle current (for example, 0.8 (A)) showing the characteristic curves (see FIG. 17) of the middle damping forces f3 and f6 and a low current (for example, 0.3 (A)) showing the characteristic curves (see FIG. 17) of the low damping forces f2 and f5 are alternately repeated.

Particularly, as applied currents on a high current side when seen from the low current (for example, 0.3 (A)), a plurality of (here two) currents, i.e., a high current (for example, 1.6 (A)) shown in the region MIN-MAX of FIG. 18C and a middle current (for example, 0.8 (A)) shown in the region MIN-MID of FIG. 18C are used.

(Cycle of Applied Current)

In the examination method for the damper of the third embodiment, the cycle of a change in the level of a current input to the damping force variable mechanism 50 is made constant as shown in FIG. 18C. Here, the constant cycle of the change in the level of the current is set at, for example, 5 (Hz) regardless of whether the amplitude of the current is high or middle.

(Application of Current and Detection of Defect by Control Box 1)

As for the current that changes between high and low levels at the above constant cycle, a control box (ECU) 1 (see FIG. 16) prepared for examination outputs a signal to generate the current. The control box 1 is connected to the damping force variable mechanism 50. When the examination method for the damper of the third embodiment is not performed (at non-examination), the controller 510 of the vehicle 500 is connected to the damping force variable mechanism 50. Therefore, when the examination method for the damper of the third embodiment is performed, the controller 510 is removed from the damping force variable mechanism 50 prior to the connection of the control box 1. Then, the control box 1 is connected to the damping force variable mechanism 50 from which the controller 510 has been removed.

Note that instead of replacing the controller 510 of the vehicle 500 with the control box 1 for examination as in the third embodiment to perform the examination method, the controller 510 may be provided with the function of the control box 1 for examination as an "examination mode" in advance.

Next, the procedure of the examination method for the damper of the third embodiment will be described.

Figure 19:
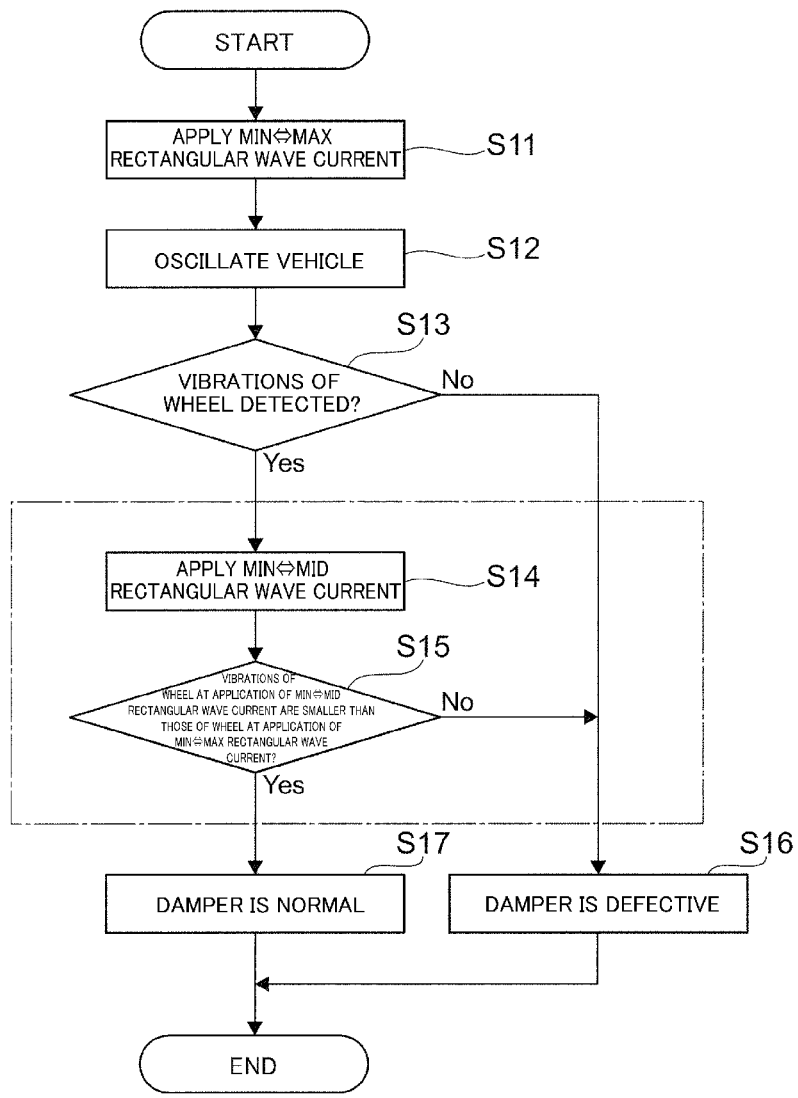
FIG. 19 is a flowchart of the examination method for the pressure damping device according to the third embodiment.

FIG. 19 is a flowchart of the examination method for the damper of the third embodiment. The flow is repeatedly performed for every prescribed timing by a control unit (not shown) constituting the control box 1 for examination.

First, the control unit of the control box 1 applies a MIN-MAX rectangular wave current (see FIG. 18C) (first fluctuation current) (step S11).

The oscillation current may be applied to the four wheels at the same time or may be applied to each of the wheels one by one. In the third embodiment, the rectangular wave current as shown in FIG. 18C is used. However, a sine wave current may be used instead. In addition, the frequency of the oscillation current is one at which the vehicle is oscillated at a frequency between a sprung resonance frequency and an unsprung resonance frequency (or a lower one of the unsprung resonance frequency and the resonance frequency of the damper), and is set at, for example, 1 to 5 Hz (5 Hz is preferable). Note that at the frequency of the oscillation current 5 Hz, a signal that changes at a frequency between the sprung resonance frequency and a lower one of the unsprung resonance frequency and the response frequency of the damper is periodically applied to the damping force variable mechanism 50 in a state in which the damper 100 is installed in the vehicle 500. The oscillation current applied in step S11 changes between MIN (for example, 0.3 (A)) and MAX (for example, 1.6 (A)).

Next, the vehicle is oscillated by an oscillation device or an examiner's hand (step S12).

Specifically, the oscillation of the vehicle is performed as follows.

While a current is applied, the vehicle 500 is oscillated up and down to stroke the damper 100 (see FIG. 18A). At a frequency of 1 to 2 Hz at which the vehicle is oscillated, the damper 100 is stroked as much as possible (see FIG. 18B). As a method for oscillating the vehicle 500, the vehicle 500 is oscillated up and down by the oscillation device or oscillated by a person's hand. When the vehicle 500 is oscillated by a person, the person opens a bonnet on a front side and presses a bulk head portion with appropriate timing so as not to deform (dents, deformation, or the like) the vehicle 500. In addition, the person opens a trunk on a rear side and presses a portion near a bumper. For example, the person is poised on an opening portion where the trunk is opened and presses the opening portion with appropriate timing using his/her weight. Further, the person opens a door, sits on a seat, and presses the seat using his/her weight to stroke front and rear wheels on one side. As described above, when the vehicle is oscillated by the person, the person vertically downwardly presses a place near a portion where the damper 100 as an examination target is installed at the load F1 to operate the damper 100 at a speed of Va (m/s). At this time, the MIN-MAX current is input to the damping force variable mechanism 50 of the damper 100.

Then, the presence or absence of the vibrations of the wheel is detected by mechanical detection based on a wheel vibration detection device (not shown) or detection based on an examiner's feeling (step S13).

Here, in order to detect a defect in the damping force variable mechanism 50 of the damper 100, the vibrations of the wheel are detected by the above wheel vibration detection device or detected in such a way that the examiner visually observes the wheel and touches the wheel by hand. If the damper 100 is not defective, it performs a hopping-like action with a change in a damping force when being stroked and is not smoothly stroked. In this case, when the examiner touches the wheel by hand, he/she feels rugged vibrations. Further, when the wheel vibration detection device is used, the vibrations are mechanically detected.

When no vibrations are detected (step S13: No), the damper 100 is determined to be defective and the flow ends.

In a case in which the damper 100 is defective and does not change a damping force, the damper 100 does not vibrate and smoothly strokes. The examiner does not feel vibrations when he/she touches the wheel.

When vibrations are detected (step S13: Yes), the control unit of the control box 1 changes the applied current from the MIN-MAX rectangular wave current to the MIN-MID rectangular wave current (see FIG. 18C) (second fluctuation current) and applies the MIN-MAX rectangular wave current (step S14). Note that although not shown in FIG. 19, the vehicle is oscillated by the oscillation device or oscillated by the examiner's hand after step S14.

That is, the control unit of the control box 1 changes from the MIN-MAX current to the MIN-MID current (for example, 0.3 (A) to 0.8 (A)), and performs the procedures of steps S11 to S13 again.

Referring back to the flowchart of FIG. 19, a determination is made as to whether the vibrations of the wheel at the application of the MIN-MID rectangular wave current are smaller than those of the wheel at the application of the MIN-MAX rectangular wave current based on the wheel vibration detection device or the examiner's feeling (step S15). As described above, the vibrations of the wheel are detected by the observation of the displacement of the wheel and the load F1.

When the vibrations of the wheel at the application of the MIN-MID rectangular wave current are greater than or equal to those of the wheel at the application of the MIN-MAX rectangular wave current (step S15: No), the damper 100 is determined to be defective and the flow ends (step S16).

When the vibrations of the wheel at the application of the MIN-MID rectangular wave current are smaller than those of the wheel at the application of the MIN-MAX rectangular wave current (step S15: Yes), the damper 100 is determined to be normal and the flow ends (step S17). Note that the step of applying the MIN-MAX rectangular wave current and the step of applying the MIN-MID rectangular wave current may be performed in a reverse order.

The functions and effects of the examination method for the damper of the third embodiment will be described with reference to FIGS. 18D and 18E.

When the damper 100 is normal, a damping force rapidly changes with a change in the generated damping force (N) of the damper 100 in FIG. 18D and the wheel greatly vibrates as indicated by parts surrounded by circles a, b, and c in FIG. 18E. On the other hand, when the damper 100 is defective, such vibrations of the wheel do not occur. Thus, based on the change occurring in the vehicle 500 with the change in the input current (the presence or absence of the generation of the vibrations of the wheel), the damping force variable mechanism 50 of the damper 100 can be examined in a state in which the damping force variable mechanism 50 is installed in the vehicle 500.

However, when a defect by which a variable width of the damping force variable mechanism 50 becomes narrow is caused in the damping force variable mechanism 50, it is possible to confirm whether the damping force variable mechanism 50 varies but is not possible to determine whether the variable width of the damping force variable mechanism 50 has become narrow. That is, only with one type of applied current, i.e., the MIN-MAX current, it is not possible to detect the defect. Therefore, in the third embodiment, a medium current (for example, 0.8 (A)) shown in the region MIN-MID of FIG. 18C is used besides a high current (for example, 1.6 (A)) shown in the region MIN-MAX of FIG. 18C.

Thus, as indicated by parts surrounded by circles d, e, and f in FIG. 18E, the normal damper 100 generates a rapid damping force to vibrate the wheel even if a change width of the applied current is made smaller (to the range of MIN (for example, between 0.3 (A)) to MID (for example, 0.8 (A))) with the change in the generated damping force (N) of the damper 100 in FIG. 18D (however, the vibrations of the wheel become smaller as the change width of the applied current reduces). Accordingly, with the application of the MIN-MID rectangular wave current, the damper 100 having a narrower variable width vibrates the wheel even if the change width of the applied current is small. In addition, the damper 100 having a narrower variable width reduces the vibrations of the wheel with the application of the MIN-MAX rectangular wave current. The above fact is summarized as follows.

(1) Normal damper:
Apply MIN-MAX rectangular wave current→Great wheel vibrations
Apply MIN-MID rectangular wave current→Small wheel vibrations
(2) Damper having narrowed variable width:
Apply MIN-MAX rectangular wave current→Small wheel vibrations
Apply MIN-MID rectangular wave current→Small wheel vibrations
(3) Damper made invariable:
No Wheel Vibrations As described above, the examination method for the damper of the third embodiment includes: the application step of periodically applying the fluctuation current, which fluctuates at a frequency between the sprung resonance frequency and a lower one of the unsprung resonance frequency and the response frequency of the damper, to the damping force variable mechanism 50 in a state in which the damper 100 is installed in the vehicle 500; the oscillation step of oscillating the vehicle 500 so as to operate the damping force variable mechanism 50 while the fluctuation current is applied to the damping force variable mechanism 50 in the application step; and the detection step of detecting the vibration state of the vehicle 500. In the application step, the plurality of types of currents is applied. In the detection step, a determination as to whether the vibration state of the vehicle 500 changes with a change in the plurality of types of currents is made.

Thus, it is understood from a difference in vibration level based on a size of a current value that the damper 100 responds to a change in the current value. Therefore, it becomes possible to detect even a defect by which a variable width becomes narrow, the defect being not detected with one type of current value, i.e., the MIN-MAX current. That is, it becomes possible to detect a defect in the damper that is allowed to vary but has a narrower variable width. As a result, the accurate determination of the damper 100 is allowed in a state in which the damper 100 is installed in the vehicle 500.

In addition, according to the examination method for the damper of the third embodiment, the damper 100 can be examined in a state in which the damper 100 is installed in the vehicle 500.

Moreover, according to the examination method for the damper of the third embodiment, the determination of the presence or absence of a change in the damping force of the damper 100 is allowed based on the pressure sense (tactile sense) of the reaction force F2 (see FIG. 16) received by the examiner. When the examiner feels the change in the reaction force F2, he/she is allowed to determine that the damping force variable mechanism 50 normally operates. On the other hand, when the examiner does not feel the change in the reaction force F2, he/she is allowed to determine that the damping force variable mechanism 50 does not normally operate.

Further, according to the examination method for the damper of the third embodiment, the reaction force F2 received by the examiner changes at a constant cycle corresponding to a change in an input current. Therefore, it is advantageous in that the change in the reaction force F2 is easily detected.

The method for examining the damper of the third embodiment is described in detail above with reference to the drawings. However, the present invention is not limited to the embodiment and may be of course appropriately modified without departing from its scope.

For example, the third embodiment uses the application of the MIN-MAX current and the application of the MIN-MID current. However, besides these currents, a plurality of types of currents may be applied. Specifically, a plurality of middle currents, i.e., a MIN-MID1 current and a MIN-MID2 current (where the MID2 current is greater than the MID1 current) for application may be changed to perform the detection according to the same examination method.

In addition, since the damper 100 of the third embodiment has the damping force variable mechanism 50 that varies a damping force according to a current value, a change in the current that fluctuates between the plurality of current values is used. However, when the damping force variable mechanism is driven by a voltage, a change in the voltage that is applied between a plurality of voltage values may be used.

Moreover, in the examination method for the damper of the third embodiment, the determination is made based on the examiner's pressure sense (tactile sense). However, the determination is not limited to the examiner's pressure sense (tactile sense). For example, the examiner may detect the presence or absence of a sound emitted from the damping force variable mechanism 50 of the damper 100 in the vehicle 500. In this case, the determination based on the examiner's pressure sense (tactile sense) may be used in combination.

EXPLANATION OF SYMBOLS

2 Detection device
50 Damping force variable mechanism
100, 200, 300, 400 Damper
500 Vehicle
F1 Vertical load

The invention claimed is:

1. An examination method for a damping force variable mechanism, the examination method comprising:
    an operation step of operating a pressure damping device in a state in which the pressure damping device is installed in a vehicle, the pressure damping device being provided with the damping force variable mechanism that changes a damping force according to an input signal; and
    a detection step of detecting an output of the vehicle due to the operation step, wherein
    the operation step comprises the sub-steps of:
        using a signal input device that is separated from the vehicle and inputs a signal to the damping force variable mechanism, the signal having a constant cycle, and
        operating the pressure damping device in a state in which the signal is input to the damping force variable mechanism by the signal input device;
    the signal input device switches between a plurality of mutually different signals and inputs a selected one of the signals to the damping force variable mechanism as the signal, and
    the detection step includes a step of determining whether the output of the vehicle changes at the constant cycle.

2. The examination method for the damping force variable mechanism according to claim 1, wherein
    the detection step includes detecting a wheel load of each wheel of the vehicle.

3. The examination method for the damping force variable mechanism according to claim 1, wherein
    the detection step includes detecting an extension/compression amount of the pressure damping device.

4. The examination method for the damping force variable mechanism according to claim 1, wherein
    the detection step includes detecting vibrations of the pressure damping device.

5. The examination method for the damping force variable mechanism according to claim 4, wherein
    an output from the vehicle is detected under a spring of the vehicle.

6. The examination method for the damping force variable mechanism according to claim 1, wherein
    the detection step includes detecting a sound of the pressure damping device.

7. The examination method for the damping force variable mechanism according to claim 1, wherein
    the operation step includes moving the vehicle with a vehicle load input mechanism.

8. The examination method for the damping force variable mechanism according to claim 7, wherein
    the vehicle load input mechanism is an elevating device that raises and lowers the vehicle.

9. The examination method for the damping force variable mechanism according to claim 7, wherein
    the vehicle load input mechanism is a step by which up-and-down movements are given to a running vehicle.

10. The examination method for the damping force variable mechanism according to claim 1, wherein
    the pressure damping device is provided with a cylinder portion having a cylinder containing a hydraulic liquid, an external cylinder provided on an outside of the cylinder, and a case provided on an outside of the outer cylinder, and the damping force variable mechanism is connected to the cylinder portion.

11. The examination method for the damping force variable mechanism according to claim 1, wherein the signal input device is at a remote location external to the vehicle.

12. The examination method for the damping force variable mechanism according to claim 1, wherein the signal input device is disconnected from the damping force variable mechanism and is not in use during driving.

13. The examination method for the damping force variable mechanism according to claim 1, the signal input device is disconnected from and not communicated with the damping force variable mechanism during driving.

14. An examination system for a damping force variable mechanism, the examination system comprising:
    a detection device that detects a wheel load of each wheel of a vehicle when a pressure damping device is operated in a state in which the pressure damping device is installed in the vehicle, the pressure damping device being provided with the damping force variable mechanism that changes a damping force according to an input signal having a constant cycle; and
    a signal input device that is separated from the vehicle and inputs a signal to the damping force variable mechanism, wherein
    the signal input device switches between a plurality of mutually different signals and inputs a selected one of the signals to the damping force variable mechanism as the signal, and
    the detection device determines whether the wheel load changes at the constant cycle.

15. An examination method for a pressure damping device of a vehicle having a damping force variable mechanism that changes a damping force according to an input signal, the examination method comprising:
    an application step of periodically applying a signal having a constant cycle at a frequency between a sprung resonance frequency and a lower one of an unsprung resonance frequency and a response frequency of the pressure damping device, to the damping force variable mechanism in a state in which the pressure damping device is installed in the vehicle;

an oscillation step of oscillating the vehicle so as to operate the damping force variable mechanism while the signal is applied to the damping force variable mechanism in the application step; and a detection step of detecting a vibration state of the vehicle, wherein a plurality of types of signals having different amplitudes is successively applied in the application step by a signal input device that is separated from the vehicle, a change in the vibration state of the vehicle is detected according to a change in the plurality of types of signals in the detection step, the signal input device switches between a plurality of mutually different signals and inputs a selected one of the signals to the damping force variable mechanism as the signal, and whether the vibration state changes at the constant cycle is determined.

16. The examination method for the pressure damping device according to claim 15, wherein the plurality of types of signals includes a first signal, the amplitude of which fluctuates between a minimum value and a maximum value, and a second signal, the amplitude of which fluctuates between the minimum value and a middle value, the middle value being set between the minimum value and the maximum value.

17. The examination method for the pressure damping device according to claim 15, wherein a vibration state under a spring of the vehicle is detected as the vibration state of the vehicle in the detection step.

18. The examination method for the pressure damping device according to claim 15, wherein the pressure damping device has the damping force variable mechanism that varies a damping force according to a current value, and the change in the signals represents a change in a current fluctuating between a plurality of current values.

19. An examination system for a damping force variable mechanism, the examination system comprising:

a detection device that detects an extension/compression amount of a pressure damping device when the pressure damping device is operated in a state in which the pressure damping device is installed in a vehicle, the pressure damping device being provided with the damping force variable mechanism that changes a damping force according to an input signal having a constant cycle; and a signal input device that is separated from the vehicle and inputs a signal to the damping force variable mechanism, wherein the signal input device switches between a plurality of mutually different signals and inputs a selected one of the signals to the damping force variable mechanism as the signal, and the detection device determines whether the extension/compression amount changes at the constant cycle.

20. An examination system for a damping force variable mechanism, the examination system comprising:

a detection device that detects a vibration of a pressure damping device when the pressure damping device is operated in a state in which the pressure damping device is installed in a vehicle, the pressure damping device being provided with the damping force variable mechanism that changes a damping force according to an input signal; and a signal input device that is separated from the vehicle and inputs a signal to the damping force variable mechanism, wherein the signal input device switches between a plurality of mutually different signals and inputs a selected one of the signals to the damping force variable mechanism as the signal.

* * * * *